United States Patent [19]
Nishino et al.

[11] Patent Number: 5,912,258
[45] Date of Patent: Jun. 15, 1999

[54] THIADIAZOLEAMIDE DERIVATIVE AND ANTI-ULCER DRUG

[75] Inventors: Chikao Nishino; Fumitaka Sato, both of Kanagawa; Tomohiro Uetake, Tokyo; Hirotada Fukunishi, Kanagawa; Nao Kojima, Tokyo, all of Japan

[73] Assignee: Shiseido Co., Ltd., Tokyo, Japan

[21] Appl. No.: 09/157,376

[22] Filed: Sep. 21, 1998

[51] Int. Cl.$^6$ ........................ C07D 289/135; A61K 31/41
[52] U.S. Cl. ........................ 514/363; 514/326; 514/342; 546/209; 546/268.7; 548/139
[58] Field of Search ............... 548/139; 514/363, 514/326, 342; 546/268.7, 209

[56] References Cited

U.S. PATENT DOCUMENTS 5,683,999  11/1997  Kondaji ................................. 514/218

FOREIGN PATENT DOCUMENTS 62-9344  1/1987  Japan ................................. G03C 1/34
63-91317  4/1988  Japan ................................. A61K 31/19

OTHER PUBLICATIONS

Chem. Ber., A. Dornow, K Fischer, Synthesen stickstoff-haltiger Heterocyclen, XXXV, pp. 72–80, 1966.
Farmaco–Ed.Sc., G. Pala, Sinfesi Di Composti Solfonilici Per 6Alogenazione Catalitica, pp. 650–666, 1958.
J.Praktische Chem., V.J. Klosa, Uber die Herstellung von Sauremiden aus Carbonsauren und Aminen bei Gegenwart von Phosphoroxychlorid, pp. 45–55, 1963.
J.Drug Res., S.Shams El–Dine, Chemical Studies in the field of Oral Hypoglycaemic Agents, pp. 203–207, 1974.

*Primary Examiner*—Robert Gerstl
*Attorney, Agent, or Firm*—Ronald R. Snider

[57] ABSTRACT

A thiadiazoleamide derivative or a salt thereof expressed by the following Formula 1:

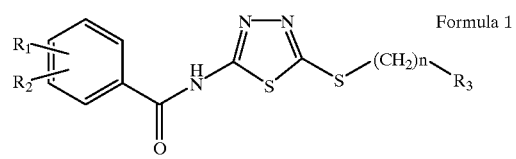

wherein each of $R_1$ and $R_2$ represents a hydrogen atom, a lower alkyl group, a lower alkoxy group, a lower alkylamino group or an alkenyloxy group; wherein when either $R_1$ or $R_2$ is a hydrogen atom, the other is not a hydrogen atom; $R_3$ represents a lower alkyl group, an aryl group, a pyridyl group or —$N(R_4)R_5$, wherein $R_4$ and $R_5$ represent lower alkyl groups or together represent a saturated heterocyclic ring having 4–8 members; wherein when $R_1$ or $R_2$ is a lower alkoxy group, $R_3$ is —$N(R_4)R_5$ or a pyridyl group; and n represents an integer of 1–3. The derivatives have anti-ulcer effect to be available for preventing or curing ulcers in mammals.

23 Claims, 5 Drawing Sheets

Reaction Formula A

Reaction Formula B

Reaction Formula C

Reaction Formula D

Reaction Formula E

Reaction Formula F

Reaction Formula G

THIADIAZOLEAMIDE DERIVATIVE AND ANTI-ULCER DRUG

RELATED APPLICATIONS

Japanese Patent Application No. 8-90628 filed on Mar. 18, 1996 is incorporated herein by reference.

FIELD OF THE INVENTION

The present invention relates to a thiadiazoleamide derivative and, in particular, to a thiadiazoleamide derivative having anti-ulcer effect.

BACKGROUND OF THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric acid secretion. Accordingly, it is important to suppress the acid secretion in order to prevent ulcer formation and to cure it.

Though various kinds of medicaments for curing ulcer have been conventionally developed, few medicaments have been known to have an effect for preventing stress ulcers from generating.

SUMMARY OF THE INVENTION

In view of the foregoing problems of the prior art, the object of the present invention is to provide a compound, which is excellent in preventing ulcer from generating, and to provide anti-ulcer drug including such a compound as a main component.

As a result of the diligent studies conducted by the inventors, it has been found that a specific thiadiazoleamide derivative is effective against various kind of ulcer due to its acid secretion inhibition as a main action mechanism.

Namely, a thiadiazoleamide derivative or its salt in accordance with the present invention is expressed by the following Formula 1:

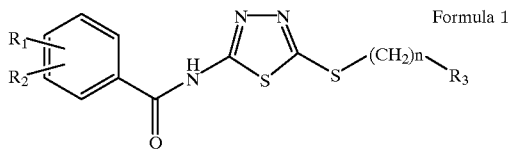

Formula 1 wherein each of $R_1$ and $R_2$ represents a hydrogen atom, a lower alkyl group, a lower alkoxy group, a lower alkylamino group; or an alkenyloxy group, wherein when either $R_1$ or $R_2$ is a hydrogen atom, the other is not a hydrogen atom;

$R_3$ represents a lower alkyl group, an aryl group, a pyridyl group, or $—N(R_4)R_5$; wherein $R_4$ and $R_5$ represent lower alkyl groups or together represents a saturated heterocyclic ring having 4–8 members; wherein when $R_1$ or $R_2$ is a lower alkoxy group $R_3$ is $—N(R_4)R_5$ or a pyridyl group; and n represents an integer of 1–3.

An anti-ulcer drug in accordance with the present invention is characterized by comprising, as an effective ingredient, said thiadiazoleamide derivative or its pharmacologically acceptable salt.

A method for treating peptic ulcers in mammals in accordance with the present invention comprises administering an effective amount of said thiadiazoleamide derivative or the pharmacologically acceptable salt thereof to said mammals.

A method for inhibiting acid secretion in stomach of mammals in accordance with the present invention comprises administering an effective amount of said thiadiazoleamide derivative or the pharmacologically acceptable salt thereof to said mammals.

A method for preventing peptic ulcers in mammals in accordance with the present invention comprises administering an effective amount of said thiadiazoleamide derivative or the pharmacologically acceptable salt thereof to said mammals.

BEST MODE FOR CARRYING OUT THE INVENTION

Figure 1:
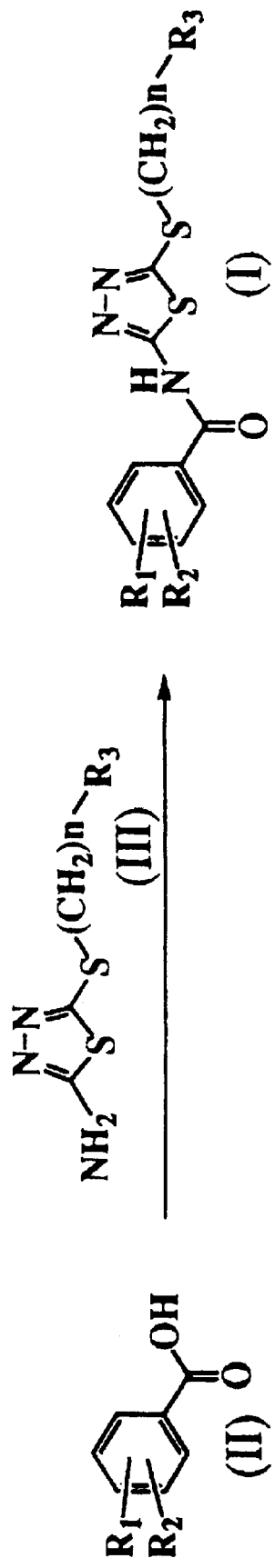
FIG. 1 shows an example of a step for manufacturing the thiadiazoleamide derivative in accordance with the present invention and FIGS. 2 to 7 shows examples of steps for manufacturing material compounds for synthesizing the thiadiazoleamide derivative in accordance with the present invention.

In the compound of the present invention, the lower alkyl group found at $R_1$ and $R_2$ represents a straight or branched alkyl group having 1 to 6 carbon atoms. Examples thereof include methyl, ethyl, n-propyl, n-butyl, isopropyl, isobutyl, 1-methylpropyl, tert-butyl, n-pentyl, 1-ethylpropyl, isoamyl, and n-hexyl groups. From the standpoint of stable anti-ulcer effect, a branched lower alkyl group is preferable, and an isobutyl or tert-butyl group is particularly preferable.

The lower alkoxy groups found at $R_1$ and $R_2$ represent the alkoxy group derived from the above-mentioned lower alkyl group. A branched lower alkoxy group is preferable and an isopropyloxy or tert-butoxy group is particularly preferable.

In the definition of $R_1$ and $R_2$, the alkenyl group in "alkenyloxy group" represents a straight or branched alkenyl group having 2 to 20 carbon atoms which comprising one or more double bond. The branched alkenyl group is preferable in view of the effect. Examples of the branched alkenyl group include prenyl, geranyl, neryl, and farnesyl groups. A preferable example of the alkenyloxy group is a geranyloxy group.

As in Formula 1, at least one of $R_1$ and $R_2$ is prefereably an alkenyloxy group, a lower alkyl group, or a lower alkoxy group.

Also, $R_1$ and $R_2$, in addition to the above-mentioned groups, may be a piperidinoalkyl or benzyloxy group. Examples of the piperidinoalkyl group include a piperidinomethyl group and a piperidinoethyl group. An alkyl group in said "piperidinoalkyl group" can be the lower alkyl group mentioned above. Also, the piperidinoalkyl and benzyloxy groups may have a substituent on its ring.

Although the lower alkyl group found at $R_3$ can be the same as defined above, a preferable example of the lower alkyl group in $R_3$ is an ethyl or n-propyl group.

In $R_3$, the aryl or pyridyl group may be an unsubstitueted or a substituted by a substituent on its unsaturated ring. For example, a phenyl, tolyl, xylyl, naphthyl, or pyridyl group can be exemplified.

Although the lower alkyl group found at $R_4$ and $R_5$ can be the same as defined above, a preferable example of the lower alkyl group in $R_4$ and $R_5$ is an ethyl group.

Also, $R_4$ and $R_5$ are combined together to form a saturated heterocyclic ring having 4–8 members. In such a case, $R_3$, which is $—N(R_4)R_5$, is preferably a piperidino group.

As in Formula 1, $R_3$ is preferably —$N(R_4)R_5$, or a pyridyl group, wherein $R_4$ and $R_5$ are the same as defined in Formula 1. Also, $R_3$ may be a lower alkyl group or an aryl group when $R_1$ or $R_2$ is an alkenyloxy or a lower alkyl group.

A preferable thiadiazoleamide derivative or its salt in the present invention may be expressed by the following Formula 2:

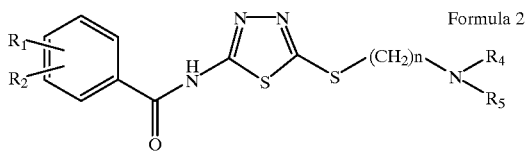

Formula 2 wherein each of $R_1$ and $R_2$ represents a hydrogen atom or a lower alkyl group; wherein when either $R_1$ or $R_2$ is a hydrogen atom, the other is a lower alkyl group; and $R_4$, $R_5$ and n are the same as defined in Formula 1.

In Formula 2, it is preferable that either $R_1$ or $R_2$ is a hydrogen atom and n is 2.

Also, a preferable thiadiazoleamide derivative or its salt in the present invention may be expressed by the following Formula 3:

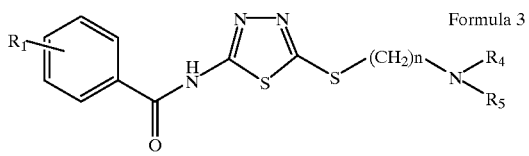

Formula 3 wherein $R_1$ represents a lower alkoxy group or a lower alkylamino group; and $R_4$, $R_5$ and n are the same as defined in Formula 1.

In Formula 3, n is preferably 2.

Also, a preferable thiadiazoleamide derivative or its salt in the present invention may be expressed by the following Formula 4:

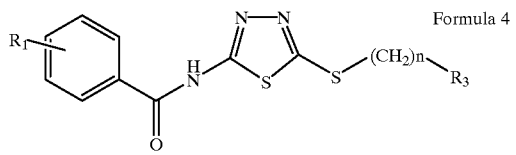

Formula 4 wherein $R_1$ represents an alkenyloxy group; $R_3$ represents —$N(R_4)R_5$ or a pyridyl group; $R_4$, $R_5$ and n are the same as defined in Formula 1.

In Formula 4, it is preferable that $R_1$ is a geranyloxy group and $R_3$ is —$N(R_4)R_5$, wherein $R_4$ and $R_5$ are the same as defined in Formula 1.

Also, a preferable thiadiazoleamide derivative or its salt in the present invention may be expressed by the following Formula 5:

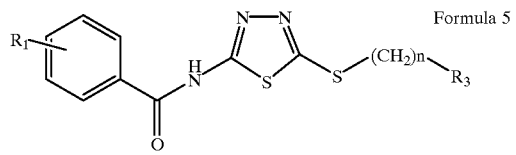

Formula 5 wherein $R_1$ represents an alkenyloxy group and $R_3$ represents a lower alkyl group or an aryl group. In Formula 5, $R_1$ is preferably a geranyloxy group.

While Compound (I) of the present invention can be manufactured by reaction formula A shown in FIG. 1, it should not be restricted thereto.

In reaction formula A, the thiadiazoleamide (I) of the present invention can be obtained from a carboxylic acid (II) and a substituted thiadiazole (III) by using a known amide forming reaction such as mixed anhydride method, acid chloride method, DCC method, CDI method, or azide method. Here, $R_1$, $R_2$, $R_3$, and n in reaction formula A are the same as shown in the definitions of Formula 1.

In the mixed anhydride method, by using an activator such as diphenyl phosphinic chloride, ethyl chloroformate, isobutyl chloroformate, or pivaloyl chloride, the carboxylic acid (II) is converted into its corresponding anhydride, and then the latter is reacted with Compound (III). As an additive, for example, an organic base such as triethylamine, pyridine or N-methylmorpholine can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of −15° C. to the reflux temperature of the solvent.

In the acid chloride method, as an activator, for example, phosphorus pentachloride, phosphorus trichloride, or thionyl chloride is used to convert the carboxylic acid (II) into the corresponding acid chloride and then the latter is reacted with Compound (III). As an additive, for example, an organic base such as triethylamine, pyridine, or N-methylmorpholine can be used. As a solvent, for example, a halogenated hydrocarbon such as dichloromethane or chloroform; an aromatic hydrocarbon such as benzene, toluene, or xylene; or an amide such as dimethylformamide or dimethylacetamide can be used. While the reaction temperature and reaction time may be changed according to the material compounds used, the reaction is usually effected at a temperature within the range of 0° C. to the reflux temperature of the solvent.

In the DCC method, as a condensing agent, for example, dicyclohexylcarbodiimide (DCC) or 1-ethyl-3-(3-dimethylaminopropyl)carbodiimide hydrochloride (WSCI) can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. If necessary, this reaction may be effected while 1-hydroxybenzotriazole (HOBt) or N-hydroxysuccinimide (HONSu) is added thereto. While the reaction temperature and reaction time may be changed according to the material compounds used, the reaction is usually effected at a temperature within the range of 0° C. to the reflux temperature of the solvent.

In the CDI method, an activator such as N,N'-carbonyldiimidazole or the like is used to convert the carboxylic acid (II) into the corresponding N-acyl derivative and then the latter is reacted with Compound (III). As an additive, for example, an organic base such as triethylamine, pyridine, or N-methylmorpholine or an inorganic base such as sodium hydride or potassium hydride can be used. As a solvent, for example, a halogenated hydrocarbon such as dichloromethane or chloroform; an aromatic hydrocarbon such as benzene, toluene or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of 0° C. to the reflux temperature of the solvent.

In the azide method, an activator such as diphenylphosphorylazide is used to convert the carboxylic acid (II) into its corresponding azide and then the latter is reacted with Compound (III). As an additive, for example, an organic base such as triethylamine, pyridine, or N-methylmorpholine can be used. As a solvent, for example, a halogenated hydrocarbon such as dichloromethane or chloroform; an aromatic hydrocarbon such as benzene, toluene or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of 0° C. to the reflux temperature of the solvent.

Specifically, for example, diphenylphosphinic chloride or pivaloyl chloride is used as an activator for the mixed anhydride method, while triethylamine is used as an additive to effect the reaction in a solvent such as chloroform or dimethylformamide at a temperature within the range of −15° C. to room temperature, thereby attaining the aimed object.

Figure 2:
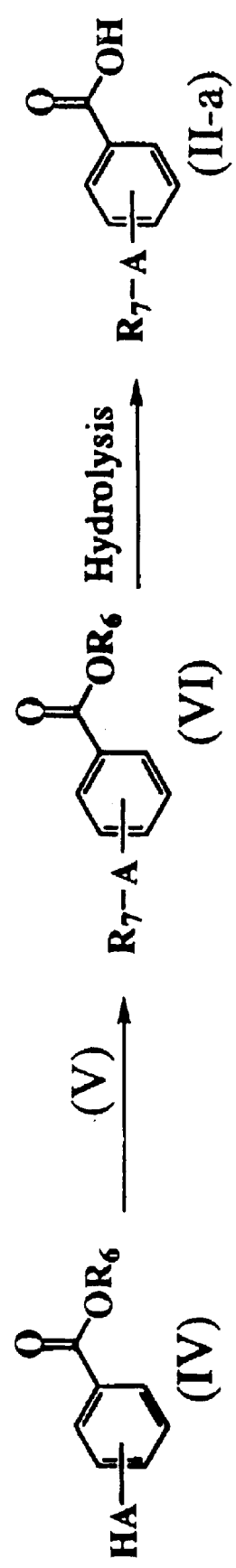

Compound (II) which is a material compound in reaction formula A can be synthesized by reaction formula B shown in FIG. 2.

In reaction formula B, A represents —O— or —NH—. Compound (V) represents $R_7$—OH, $R_7$—X or an alkene having $R_7$ as a basic structure. $R_7$ is a branched lower alkyl group or a branched alkenyl group, while X represents a halogen atom. $R_6$ represents a carboxyl-protecting group which may be a lower alkyl group such as a methyl, ethyl, or tert-butyl, phenacyl, or trichloroethyl group as long as no problem occurs in the subsequent reaction.

In reaction formula B, Compound (IV) is reacted with Compound (V) and then hydrolyzed so as to synthesize a carboxylic acid (II-a).

The first step of this reaction can be effected under an acidic condition in the case where Compound (V) is $R_7$—OH or an alkene having $R_7$ as a basic structure. As a catalyst, for example, a mineral acid such as sulfuric acid or hydrochloric acid; an organic acid such as p-toluenesulfonic acid; or Lewis acid such as boron trifluoride-etherate can be used. As a solvent, for example, a halogenated hydrocarbon such as dichloromethane or chloroform; an aromatic compound such as benzene, toluene, xylene, or pyridine; an ether such as tetrahydrofuran or dioxane; or an amide such as N,N-dimethylformamide or N,N-dimethylacetamide can be used. When Compound (V) is alcohol, Compound (V) itself can be used as a solvent. While reaction temperature and reaction time may be changed according to the material compounds used, the reaction is usually effected at a temperature within the range of 0° C. to the reflux temperature of the solvent.

Specifically, for example, 95% sulfuric acid or the like is used as acidic catalyst to effect the reaction in a solvent such as dichloromethane while being cooled with ice, thereby attaining the aimed object.

The first step of this reaction can be effected in the presence of a base in the case where Compound (V) is $R_7$—X. Sodium amide, triethylamine, sodium hydride, sodium hydroxide, potassium carbonate, barium oxide, silver oxide, or the like can be used therefor. Also, a catalytic amount of potassium iodide can be added thereto. As a solvent, for example, an alcohol such as methanol, ethanol, or butanol; an aromatic compound such as benzene, toluene, xylene, or pyridine; an ether such as diethylether, tetrahydrofuran, or dioxane; an amide such as dimethylformamide or dimethylacetamide; or a ketone such as acetone can be used. While reaction temperature and reaction time may be changed according to the material compounds used, the reaction is usually effected at a temperature within the range of 0° C. to the reflux temperature of the solvent.

Specifically, for example, Compound (IV) is dissolved in tetrahydrofuran or N,N'-dimethylformamide and, after sodium hydride as a base is added and stirred therein, the alkenyl halide is added thereto so as to effect a reaction at a temperature within the range of room temperature to the reflux temperature of the solvent, thereby attaining the aimed object.

In the reaction at the second step, the ester (VI) is hydrolyzed in the presence of an acid or a base so as to synthesize the carboxylic acid (II-a). Hydrochloric acid, sulfuric acid, p-toluenesulfonic acid or the like can be used as the acid, while sodium hydroxide, potassium hydroxide, potassium tert-butoxide or the like can be used as the base. As a solvent, a carboxylic acid such as formic acid or acetic acid; an alcohol such as methanol or ethanol; water; or a mixed solvent thereof can be used. While the reaction temperature and reaction time can be changed according to the material compounds used, the reaction is usually effected at a temperature within the range of 0° C. to the reflux temperature of the solvent.

Specifically, for example, the ester (VI) is dissolved in alcohol such as methanol or ethanol and then an aqueous solution including sodium hydroxide or potassium hydroxide is added thereto so as to effect a reaction at a temperature within the range of room temperature to the reflux temperature of the solvent, thereby attaining the aimed object.

Figure 3:
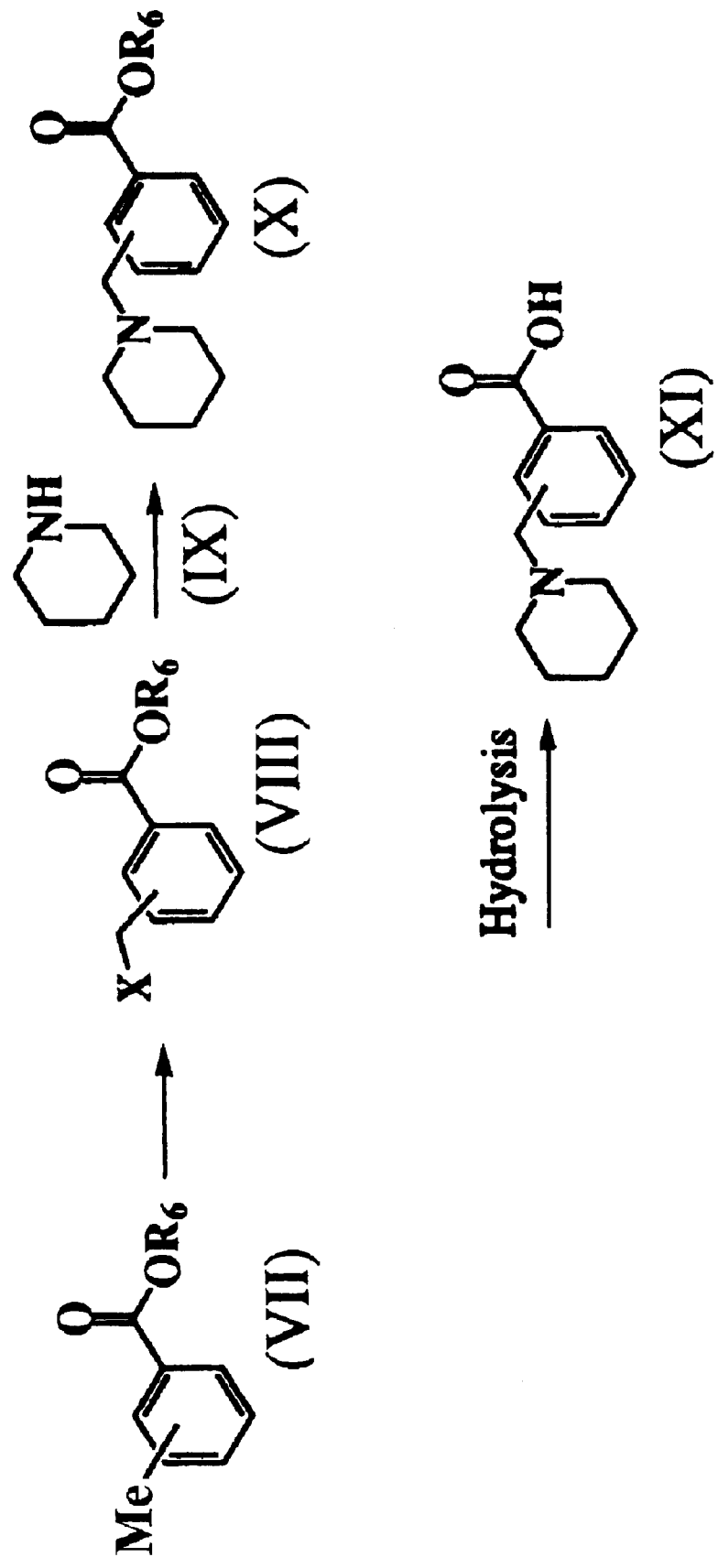
Figure 4:
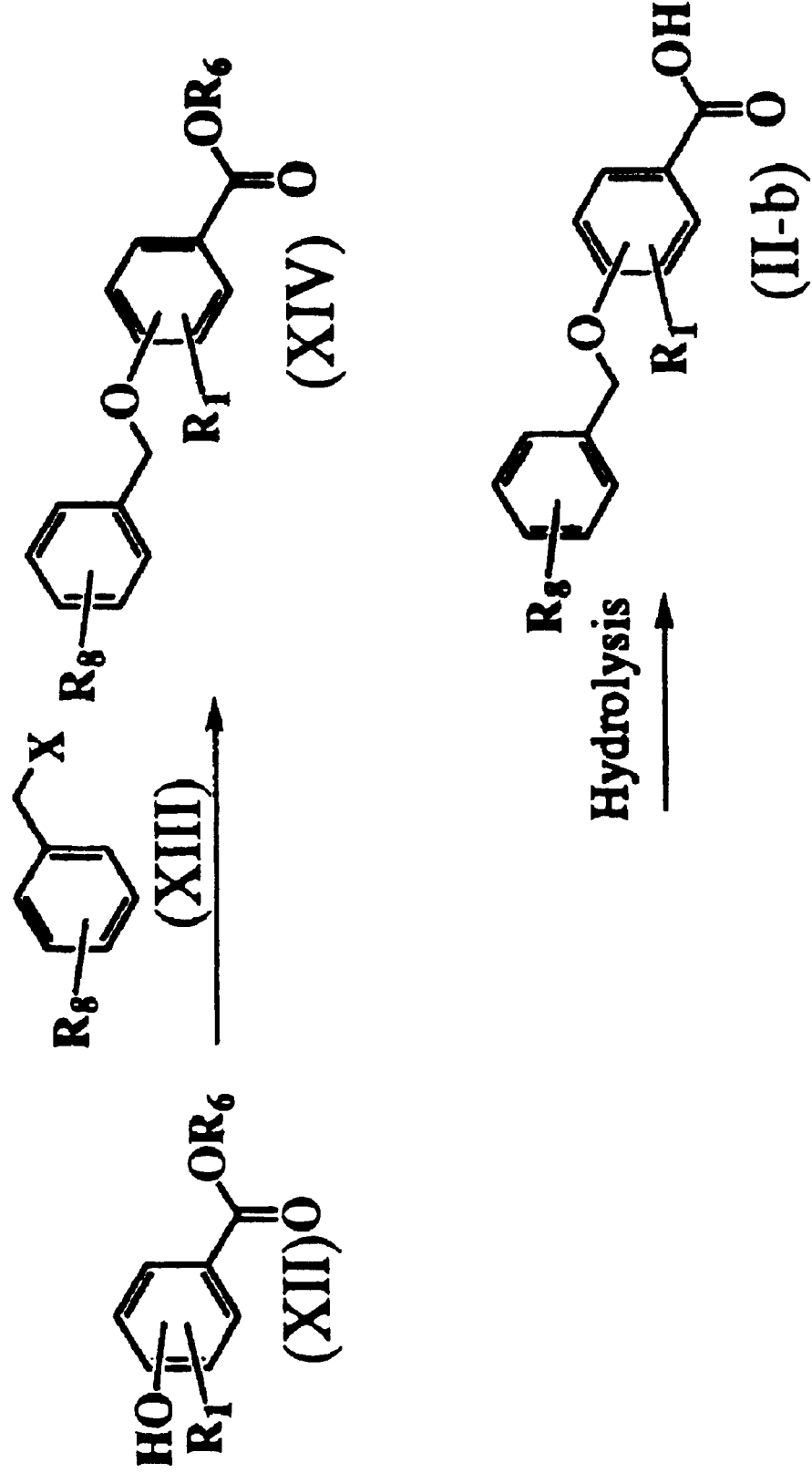

Also, Compound (XI) or Compound (II-b) synthesized by reaction formula C or reaction formula D shown in FIG. 3 or FIG. 4 may be used as the material compound (II) in reaction formula A.

In reaction formula C, X represents a halogen atom. $R_6$ represents a carboxyl-protecting group, which may be a lower alkyl group such as a methyl, ethyl, or tert-butyl, phenacyl, or trichloroethyl group as long as no problem occurs in the subsequent reaction.

At the first step in reaction formula C, a benzyl halide (VIII) can be obtained by halogenating the methyl group of Compound (VII).

As a reagent used in this reaction, for example, N-bromosuccinimide (NBS), N-chlorosuccinimide (NCS), N-halogenocaprolactam, 1,3-dihalogeno-5,5-dimethylhydantoin or the like can be used. As a solvent, a halogenated hydrocarbon such as dichloromethane or chloroform; an aromatic compound such as benzene, toluene, xylene, or pyridine; an ether such as tetrahydrofuran or dioxane; or an amide such as N,N-dimethylformamide or N,N-dimethylacetamide can be used. If necessary, this reaction may be effected while a peroxide such as benzoyl peroxide is added thereto. While the reaction temperature and reaction time may be changed according to the material compounds used, the reaction is usually effected at a temperature within the range of 0° C. to the reflux temperature of the solvent.

Specifically, for example, into Compound (VII) dissolved in dichloromethane, N-bromosuccinimide added and the reaction is effected in the presence of catalyst at reflux temperature, thereby attaining the aimed object.

At the second step in reaction formula C, Compound (X) can be obtained by reacting piperidine (IX) with a benzyl halide (VIII) in the presence of a base.

The reaction of the halide and the amine at the second step can be effected under a reaction condition similar to that of the first step in reaction formula B.

Also, the hydrolysis at the third step of reaction formula C can be effected under a reaction condition similar to that of the second step in reaction formula B.

In reaction formula D shown in FIG. 4, a hydroxy compound (XII) is reacted with a benzyl halide (XIII) in the presence of a base, and then hydrolyzed so as to obtain a carboxylic acid (II-b). Here, in reaction formula D, $R_1$ is defined as mentioned above, while X represents a halogen atom. $R_8$ represents a hydrogen atom, a halogen atom, a cyano, a nitro, a lower alkyl or a lower alkoxy group. $R_6$ represents a carboxyl-protecting group which may be a lower alkyl group such as a methyl, ethyl, or tert-butyl, phenacyl, or trichloroethyl group as long as no problem occurs in the subsequent reaction.

The benzylation at the first step of reaction of reaction formula D can be effected under a reaction condition similar to that of the second step in reaction formula C, while the hydrolysis at the second step of reaction formula D can be effected under a reaction condition similar to that of the second step in reaction formula B.

Figure 5:
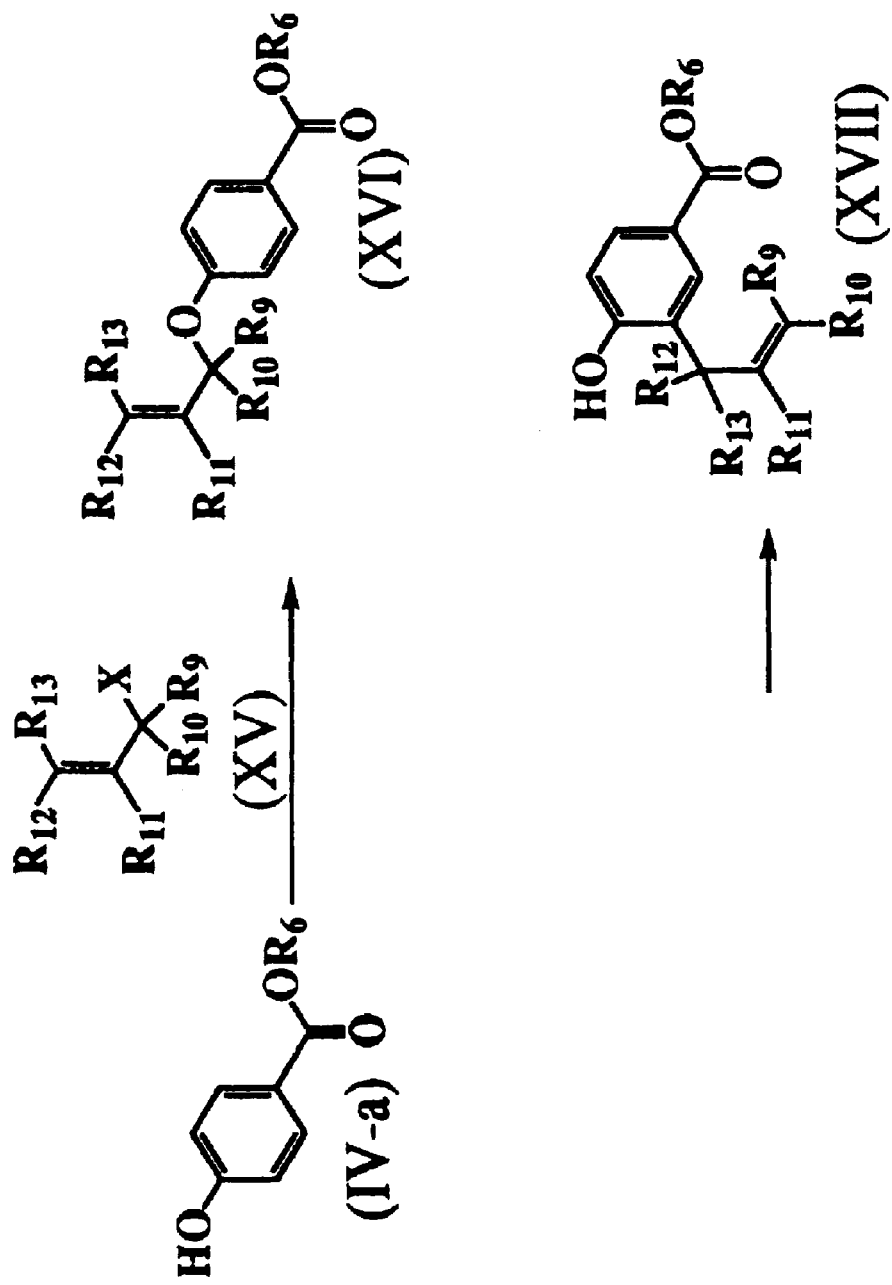

The material compound (XII) in reaction formula D may be commercially available or synthesized. For example, Compound (XVII), wherein $R_1$ in formula (XII) is a lower 2-alkenyl group, can be manufactured by reaction formula E shown in FIG. 5. Further, from Compound (XVII), Compound (XVIII), wherein $R_1$ in formula (XII) is a lower alkyl group, can be manufactured by reaction formula F shown in FIG. 6.

At the first step of reaction formula E, Compound (IV-a) is reacted with a halide (XV) in the presence of a base to obtain Compound (XVI). In reaction formula E, $R_9$, $R_{10}$, $R_{11}$, $R_{12}$, and $R_{13}$ represent hydrogen atoms or lower alkyl groups individually, while X represents a halogen atom. $R_6$ represents a carboxyl-protecting group which may be a lower alkyl group such as a methyl, ethyl, or tert-butyl, phenacyl, or trichloroethyl group as long as no problem occurs in the subsequent reaction.

As a base in this reaction, for example, an inorganic base such as potassium carbonate, potassium hydroxide, sodium hydroxide, or sodium hydride, or an organic base such as triethylamine or pyridine can be used. Specifically, for example, potassium carbonate is used as the base so as to effect a reaction in a solvent such as acetone or dimethylformamide at a temperature within the range of room temperature to the reflux temperature of the solvent, thereby attaining the aimed object.

At the second step of reaction formula E, Compound (XVI) is subjected to Claisen rearrangement reaction so as to obtain Compound (XVII). This reaction is effected in or without the presence of a high-boiling solvent under normal or high pressure. Examples of the solvent include phenyl ether and N,N-dimethylaniline. While the reaction temperature and reaction time may be changed according to the material compounds used, the reaction is normally effected at a temperature within the range of 100° C. to 200° C.

Figure 6:
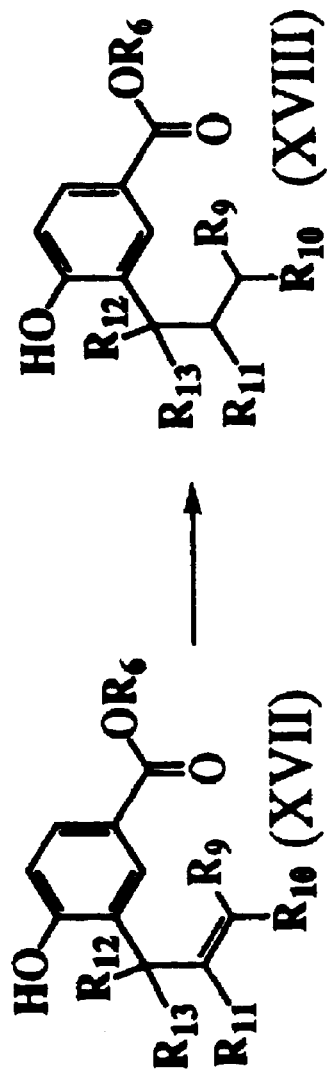

As shown in reaction formula F of FIG. 6, Compound (XVIII) can be obtained by hydrogenation of Compound (XVII) obtained by the foregoing reaction formula E. In formula F, $R_9$, $R_{10}$, $R_{11}$, $R_{12}$, $R_{13}$, and $R_6$ are defined as those in reaction formula E.

When this reaction is effected under a catalytic reduction condition, as a catalyst, palladium, platinum, nickel, rhodium, ruthenium, or the like can be used. Specifically, for example, by using palladium-carbon, in a solvent such as ethanol, ethyl acetate, or tetrahydrofuran, under a hydrogen gas atmosphere, a reaction is effected at a temperature within the range of room temperature to the reflux temperature of the solvent, thereby attaining the aimed object.

Figure 7:
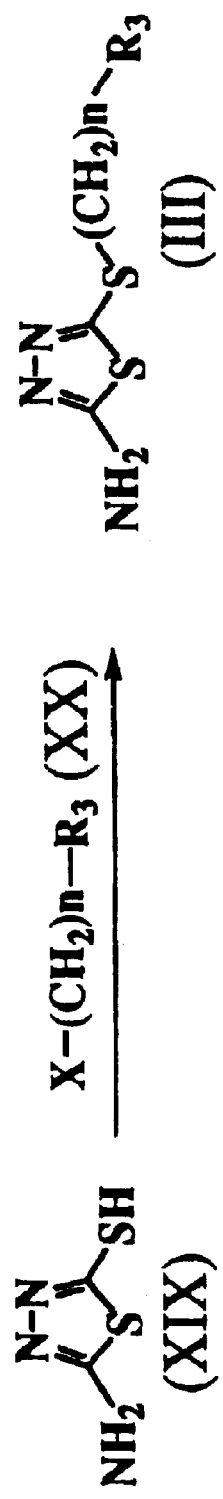

Compound (III), which is the other material compound of reaction formula A, can be manufactured, as shown in reaction formula G of FIG. 7. In reaction formula G, $R_3$ and n are defined as Formula 1, while X represents a halogen atom.

In reaction formula G, Compound (XIX) is reacted with a halide (XX) in the presence of a base so as to obtain Compound (III).

This reaction can be effected under a reaction condition similar to that of the second step in reaction formula C.

Among the material compounds used in the above-mentioned reaction formulae, those with no preparation methods described may be commercially available or easily synthesized by using a known method.

Also, examples of salts of the thiadiazoleamide derivative (I) of the present invention with an acid include salts with inorganic acids such as hydrochloric acid, hydrobromic acid, sulfuric acid, or phosphoric acid and salts with organic acids such as acetic acid, propionic acid, citric acid, lactic acid, oxalic acid, maleic acid, fumaric acid, succinic acid, tartaric acid, or methane sulfonic acid. These salts can be easily manufactured by a common method.

The thiadiazoleamide derivative in accordance with the present invention has a strong effect against stress ulcer and an excellent effect for suppressing gastric acid secretion. Furthermore, it has a high safety. Accordingly, it is useful as a medicament for curing and preventing peptic ulcer in mammals, and particularly, in man.

When the compound of the present invention is administered as a medicament for curing and preventing peptic ulcer, it may be administered orally as tablet, powder, granule, capsule, syrup, or the like as well as parenterally as suppository, injection, external drug, instillation or the like. While the amount of administration may be outside of the range mentioned below according to the degree of symptom, personal difference, age, kind of ulcer, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methylcellulose, gum arabic, tragacanth, gelatin, shellac, hydroxypropyl cellulose, hydroxypropyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When preparing an injection, if necessary, a pH-adjusting agent, a buffer, a stabilizer, a solubilizer, and the like are added to the main medicament and then a normal method is used to form subcutaneous, intramuscular, and intravenous injection drugs.

EXAMPLES

The present invention will be explained in the following according to examples. However, the present invention should not be restricted thereto.

First, test methods used for evaluating these examples as an anti-ulcer drug will be explained.

WIS: Restraint and Water Immersion Stress-Induced Ulcer Inhibition Test (i) Meaning The degree of inhibition of the stress ulcer formation is tested.

(ii) Method

Male Crj:SD or Slc:SD rats (6 to 7-weeek-old) were fasted overnight, but allowed free access to water. Each group has 5 to 8 of these rats. The sample compound was dissolved or suspended in an aqueous solution of 0.3% sodium carboxymethylcellulose or 0.05% Tween 80 and then was orally administered (100 mg/10 ml/kg). To a control group, the vehicle was administered. 10 minutes later, the rats were placed in a stress cage and immersed to the level of xiphoid process in a water bath (21° C.) for 7 hours. At the end of the stress, the rats were sacrificed by inhalation of ether or carbon dioxide. Then, the stomach of each was removed, inflated by injecting 10 ml of 5% formalin neutral buffer solution, and immersed in 1% formalin neutral buffer solution for 30 minutes or more to be fixed. The stomach was incised along the greater curvature and then the length of each erosion in the glandular portion was determined under dissecting microscope. The sum of the length of erosions per stomach was defined as ulcer index (UI).

(iii) Judgment Standard

The effect obtained when 100 mg/kg of the sample compound had been administered was expressed as ulcer formation inhibitory rate (%) as follows:

ulcer formation inhibitory rate (%)={1-(UI in sample group/UI in control group}×100

VOL, TAO: Acid Secretion Inhibition Test in vivo (i) Meaning

Inhibitory effect on acid secretion in vivo is confirmed.

(ii) Method

Male Crj:Donryu rats (7-week-old) were fasted overnight but allowed free access to water. In each group, 8 to 10 of these rats were used under urethane anesthesia (1.25 g/kg). The sample compound dissolved or suspended in an aqueous solution of 0.5% sodium carboxymethylcellulose or 0.05% Tween 80 was orally administered (100 mg/10 ml/kg). 30 minutes later, the abdomen of each was incised and the pylorus was ligated. 30 minutes after the ligation, 30 mg/kg of histamine dissolved in physiological saline was subcutaneously administered and, 3 hours thereafter, the rat was sacrificed with carbon dioxide. Immediately thereafter, each stomach was removed and the gastric contents were collected and each volume was determined. The total acid output was determined by titration of the gastric juice with 0.1N NaOH.

(iii) Judgment Standard

With respect to the gastric juice volume (VOL) and the total acid output (TAO), the effects obtained when 100 mg/kg of the sample compound had been administered were expressed as their respective inhibitory rates (%) as follows:

each inhibitory rate (%) {1-(value in sample group/value in control group)}×100

CAP: Acid Secretion Inhibition Test in vitro (i) Meaning

The acid secretion inhibitory activity in a cell level is studied. It can also be used for studying the mechanism of the effect.

(ii) Method (ii)-(a) Preparation of isolated gastric gland suspension

First, an isolated gastric fundic gland sample was prepared. Namely, a male Japanese White rabbit (2.5 to 3 kg) was anesthetized to death with Nembutal™ and then the abdomen was incised. Immediately thereafter, the stomach was removed and, after its pyloric and cardiac antrum were severed, incised along its greater curvature into two sheets. The gastric contents adhering to the mucosal surface was washed out with ice-cooled PBS (−) and then carefully washed therein. The gastric wall was spread on a cork board with its mucosal surface facing up and the feed and mucus thereon were completely removed with sterile gauze. The mucosa was separated therefrom by a spatula and then collected in ice-cooled PBS (−). After being washed twice with PBS (−), the mucosa was minced into 2–3 $mm^3$ pieces by scissors. These pieces were further washed twice with a nutrient solution. The nutrient solution comprises 132.4 mM of NaCl, 5.4 mM of KCl, 5 mM of $Na_2HPO_4 \cdot 12H_2O$, 1 mM of $NaH_2PO_4 \cdot 2H_2O$, 1.2 mM of $MgSO_4$, 1 mM of $CaCl_2$, 25 mM of HEPES, 2 mg/ml of glucose, and 1 mg/ml of BSA. Into 70 ml of the nutrient solution containing 1 mg/ml of collagenase, minced mucosal pieces were dispersed and intensely stirred in a conical flask with a stirrer at 37° C. for 40 to 60 minutes. During this period, 100% $O_2$ was sprayed on the nutrient solution surface and the pH was appropriately measured such that it was immediately adjusted to pH 7.4, when the value was therebelow, with a base. The nutrient solution was added to the reaction solution so as to attain the total amount of about 200 ml. After being filtered through a mesh, the suspension was divisionally introduced into 50 ml centrifuge tubes and left for 15 minutes such that gastric fundic gland was deposited. The supernatant was repeatedly removed by an aspirator, dispersed in the nutrient solution, and then left such that the gastric fundic gland was washed three times. At this time, without using a pipette, the suspension was alternately introduced into two centrifuge tubes so as to effect dispersion. The number of cells was counted under microscope and adjusted to $1.6 \times 10^6$ cells/ml.

(ii)-(b) [$^{14}$C]-aminopyrine uptake test

Then [$^{14}$C]-aminopyrine uptake test was performed. After an Eppendorf tube was weighed, 10 μl (final concentration: $10^{-5}$ M) of histamine dissolved in the above-mentioned nutrient solution, 10 μl (final concentration: $10^{-5}$ M) of the test compound dissolved in DMSO, and 10 μl (final concentration: 0.05 μCi/ml) of [$^{14}$C]-aminopyrine diluted with the nutrient solution were introduced therein and then 970 μl of the isolated gastric fundic gland suspension prepared above were added thereto. Subsequently, this mixture was shaken at 37° C. for 40 minutes at 125 cycles/minute. After being centrifuged for 30 minutes 200 μl of its supernatant was collected into a mini-vial, while the rest was removed by an aspirator. The gland pellet was completely dried as the tube with its lid being opened was kept for one night in a drying oven at 80° C. and then the weight was determined at room temperature. Then 100 μl of 1N KOH was added thereto an the tube with its lid being closed was treated at 60° C. for 1 to 2 hours so as to dissolve the pellet. Then, the contents thereof were transferred to a mini-vial. Into the mini-vial containing the supernatant or gland pellet, 4 ml of Atomlite™ was added and then the radioactivity was measured by a liquid scintillation counter. Here, after the radioactivity of the gland pellet was corrected by using a sample in which 20 mM of NaSCN was added so as to cancel the hydrogen ion concentration gradient, the integration ratio of aminopyrine specifically trapped by the gland pellet was calculated. This experiment was performed in duplicate.

(ii)-(c) Calculation of the accumulation rate of aminopyrine

Here, its principle will be briefly explained. In the isolated gastric fundic gland, acid is accumulated in a space between its secretory tubule and intraglandular cavity. Aminopyrine is weak base (pKa=5.0) and nonionic in a neutral solution so as to freely pass through the cell membrane, whereas it is ionized in an acidic solution and thus cannot pass through the cell membrane due to its electric charge. Therefore, aminopyrine is accumulated in a closed acidic space within the isolated gastric fundic gland. In view of this characteristic, the accumulation rate (R) of aminopyrine is calculated by the following equation:

R={(corrected radioactivity of precipitate)/(radioactivity of supernatant)}×{200/(mg dry weight of gland pellet)}

(iii) Judgment Standard

The effect of the sample compound at the final concentration of $10^{-5}$ M was expressed by acid secretion inhibitory rate (%) as follows:

Acid secretion inhibitory rate (%)={1-(R in sample group/R in control group)}×100

PD: Gastric Mucosal Integrity Test (i) Meaning

There is a possibility that the anti-ulcer mechanism of the compounds which were effective in the experimental ulcer model may be attributed to adaptive cytoprotection, which means exhibiting of apparent anti-ulcer effect due to increase in the amount of endogenous prostaglandins in the gastric mucosa caused by necrotizing agents. In this case, since the sample compound has a necrotizing effect, it is inappropriate as an anti-ulcer medicament.

Therefore, the gastric mucosal potential difference (PD), which reflects the integrity of the gastric mucosa, is measured so as to confirm that the sample compound has no damaging effect on gastric mucosa, which is toxicity at gastric mucosal level.

(ii) Method

Male Crj:SD rats (7 to 8-week-old) were fasted overnight, but allowed free access to water, and then, under urethane anesthesia (1.25 g/kg, i.p.), fixed to a cork board on its back. The abdomen of each rat was incised, and a small incision was made in the forestomach. Then, the inside of the stomach was washed with physiological saline heated at 37° C. From the forestomach, along the greater curvature thereof, the stomach was incised without damaging blood vessels. After the height of the cork board was adjusted on a jack, the stomach was mounted on ex vivo chamber. The area of the gastric mucosa exposed to the inside of this chamber was 2.5 cm². The inside of the chamber was perfused with physiological saline warmed at 37° C. by micro tube pump. By using an agar bridge containing 3M KCl, the potential difference between the chamber and the abdominal cavity was measured by a PD meter. Here, the rectal temperature was measured to control the body temperature during the experiment. After the PD was sufficiently stabilized, the perfusate was stopped and then 100 mg/10 ml/kg of the sample compound dissolved or suspended in an aqueous solution of 0.5% sodium carboxymethylcellulose or 0.05% Tween 80 was administered into the chamber, while PD was recorded for 60 minutes. To a control, the vehicle was administered.

(iii) Judgment Standard

The change in PD during 60 minutes after the administration of 100 mg/kg of the sample compound was collectively studied and, with reference to the positive control, classified into 5 levels as follows:

5: Same as the control with no recognizable damage at all.

4: Though a slight PD-decreasing tendency suggesting a slight possibility of mucosal damage is found, there is no problem.

3: Though a weak decrease in PD and a possibility of a weak mucosal damage is recognized, there is no substantial problem.

2: Medium degree of decrease in PD is found and a mucosal damage is recognized.

1: Heavy degree of decrease in PD is found and a remarkable mucosal damage is recognized.

AT: Single Dose Toxicity Pretest (i) Method

Male Slc:ICR mice (5-week-old) were used. Each group has 3 to 5 mice and each mouse was fasted, but allowed free access to water, for 4 to 5 hours from 9 a.m. in the test day. Then, 2,000 mg/10 ml/kg of the sample compound dissolved or suspended in an aqueous solution of 0.5% sodium carboxymethylcellulose was orally administered thereto. To a control, only the vehicle was administered. The behavior and symptom were observed at each of 15 minutes, 30 minutes, 1 hour, 2 hours, and 3 hours after the administration and then daily till one week thereafter. The body weight was measured before and after the fasting as well as at the same time everyday. The dead animals were immediately subjected to autopsy and their organs were observed by naked eyes. Also, the living animals were sacrificed with ether or carbon dioxide one week after the administration and then their organs were observed by naked eyes.

(ii) Judgment Standard

The toxicity at the single dose of 2,000 mg/kg of the sample compound was expressed as being classified into 5 levels.

5: Mortality rate is 0%; no toxicity is found at all both in behavior and organs.

4: Mortality rate is 0%; while no toxicity is found in organs, slight toxicity is observed in behavior and body weight increase.

3: While there is a dead animal (though not all the animals are dead), no toxicity is found in organs.

2: Regardless of whether there is a dead animal or not, toxicity is found in organs.

1: All the animals are dead.

MTT: Cell Damaging and Protecting Effect Test (i) Meaning

It is confirmed that there is no toxicity in cell level. Those having toxicity in cell level are inappropriate as an anti-ulcer drug. Also, it can be confirmed that the effects of the sample compounds in other cell level tests do not result from their toxicity.

(ii) Method

A male Japanese White rabbit (2.5 to 3 kg) was anesthetized to death by Nembutal™ and, immediately thereafter, its stomach was removed. The greater curvature of the stomach was incised so as to remove the stomach contents therefrom. After the mucosal surface was washed with HBSS (Hank's Balanced Salt Solution), the stomach in ice-cooled HBSS was transferred to a laboratory. Then, after the pyloric antrum was removed, the gastric corpus mucosa was separated by a spatula and then minced into 2 to 3 mm pieces in BME (Basal Medium Eagle). Thereafter, these pieces were shaken at 120 to 130 cycles/minute for 15 minutes at 37° C. in BME 60 ml containing 280 U/ml of dispase and 30 to 50 U/mil of collagenase. Here, the concentration of collagenase was appropriately changed for each lot in view of the state of cells. The pieces were washed twice with EBSS (Earle's Balanced Salt Solution) containing 1 mM of EDTA and then shaken in MEM (Minimum Essential Medium) containing 1 mM of EDTA at 37° C. for 5 minutes. Subsequently, they were shaken in the dispase and collagenase having the same concentrations as those mentioned above for 15 minutes so as to remove the supernatant and then further shaken at 37° C. for 50 to 60 minutes at 120 to 130 cycles/minute. Then, after being washed twice with HBSS, Ham F12 containing 2% of Ultrocer G™ was used to attain the concentration of $1 \times 10^6$ cells/ml. Thus formed suspension was dispensed in each well of a 96-well plate by 200 μl. The plate was incubated in the atmosphere composed of 5% $CO_2$ and 95% air at 37° C. for three days so as to attain a confluent state and then subjected to MTT assay.

The sample compound was dissolved in DMSO so as to attain a concentration of $10^{-2}$ M and then diluted with HBSS containing 2% of Ultrocer G™ so as to attain a final concentration of $10^{-4}$ M. To each group, which 8 wells were used for, 10 μl of MTT reagent was added immediately after 100 μl of the medium in each well was exchanged for same volume of the resulting solution of the sample compound. After being incubated in an atmosphere composed of 5% $CO_2$ and 95% air at 37° C. for 4 hours, thus formed solution was centrifuged and then its supernatant was discarded. Subsequently, 100 μl of 100% ethanol was added to the residue so as to dissolve MTT formazan. Then, the absorbance (OD: 570 to 630) was measured by a microplate reader. This method utilizes a phenomenon in which MTT is changed to MTT formazan only by mitochondria of living cells so as to change color.

(iii) Judgment Standard

The cell damaging or cell protecting effect of the sample compound at the final concentration of $10^{-4}$ M was expressed as cell damaging rate (%) as follows:

cell damaging rate (%)={1-(absorbance in sample group/absorbance in control group)}×100

Accordingly, the smaller value is better in the cell damaging rate.

Based on the foregoing effect tests and safety tests, the example compounds of the present invention were studied.

Compound Group 1

The present compound group has a structure shown by Formula 2 mentioned above. As the thiadiazoleamide derivatives corresponding to this group, the following compounds were tested. The results of their effect tests and safety tests are shown in TABLE 1.

Example 1:

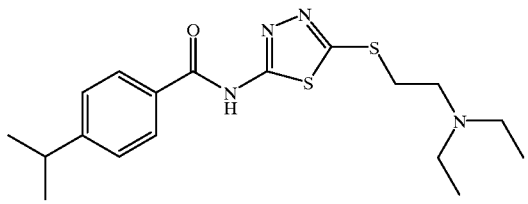

Example 2:

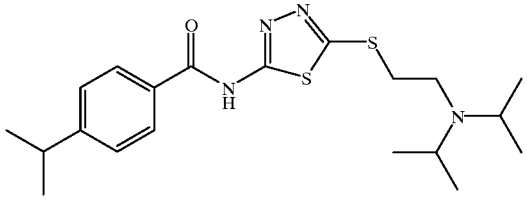

Example 3:

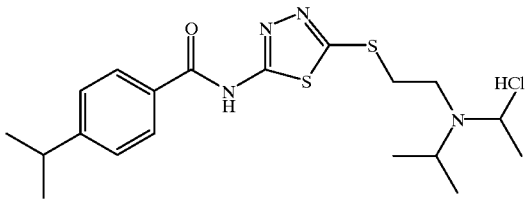

Example 4:

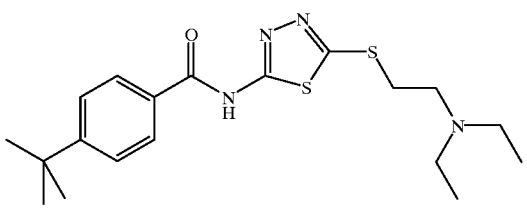

Example 5:

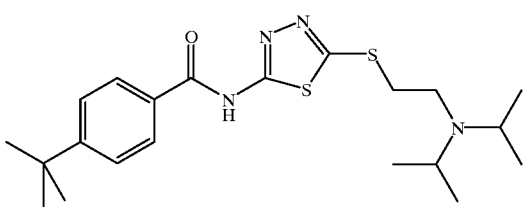

Example 6:

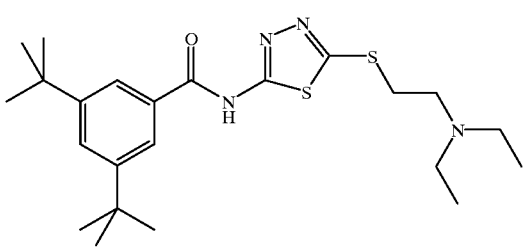

TABLE 1

| Example | Anti-ulcer Tests | | Tests for Safety | | |
|---|---|---|---|---|---|
| No. | WIS | CAP | PD | AT | MTT |
| 1 | 83 | 101 | 3 | | 22 |
| 2 | 80 | 100 | 5 | 5 | -77 |
| 3 | 96 | 104 | | | -75 |
| 4 | 79 | 100 | 3 | | 22 |
| 5 | 63 | 100 | | | -19 |
| 6 | 81 | 100 | | | 58 |

As can be seen from Examples 1 to 6 in TABLE 1, the compounds expressed by the above-mentioned Formula 2 has an excellent anti-ulcer effect and acid secretion inhibition effect from the results of WIS and CAP. The compounds are also excellent in safety. As to $R_1$ and $R_2$, while a high anti-ulcer effect is obtained in general when a lower alkyl group is introduced onto the benzene ring as shown in Examples 1 to 5, sufficient effects are obtained when two alkyl groups are introduced as shown in Example 6.

Compound Group 2

The thiadiazoleamide derivatives in accordance with this group, as against that $R_1$ is a lower alkyl group in the compound group 1 mentioned above, has a basic structure in which $R_1$ is a lower alkoxy group or a lower alkylamino group as shown in Formula 3.

As the thiadiazoleamide derivatives corresponding to this group, the following compounds were tested. The results are shown in TABLE 2.

Example 7:

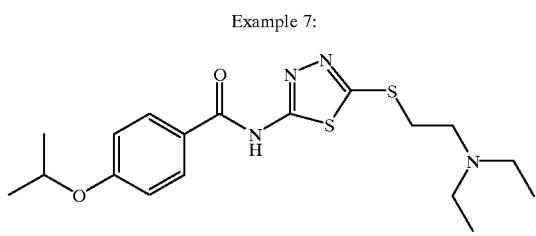

Example 8:

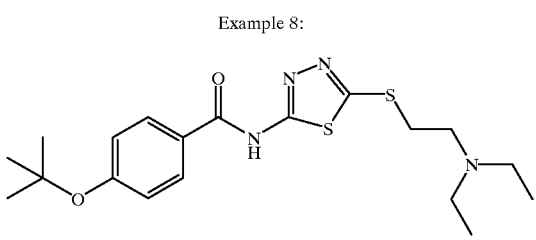

Example 9:

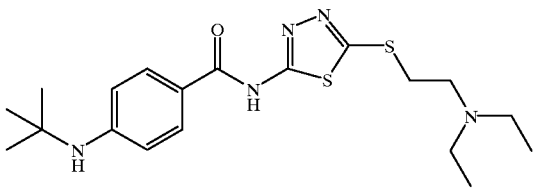

TABLE 2

| Example No. | Anti-ulcer Tests | | Test for Safety |
|---|---|---|---|
| | WIS | CAP | MTT |
| 7 | 76 | 97 | 46 |
| 8 | 66 | 99 | −11 |
| 9 | 51 | 2 | −107 |

As can be seen from the foregoing Examples, when $R_1$ is a lower alkoxy group or a lower alkylamino group, anti-ulcer effect, acid secretion inhibition effect, and safety can be exhibited sufficiently.

Compound Group 3

The thiadiazoleamide derivatives in accordance with this compound group 3 has a basic structure in which $R_1$ is a lower alkenyloxy group and $R_3$ is a group containing nitrogen such as —$N(R_4)R_5$ or a pyridyl group as shown in Formula 4.

As the thiadiazoleamide derivatives corresponding to this group, the following compounds were tested.

Example 10

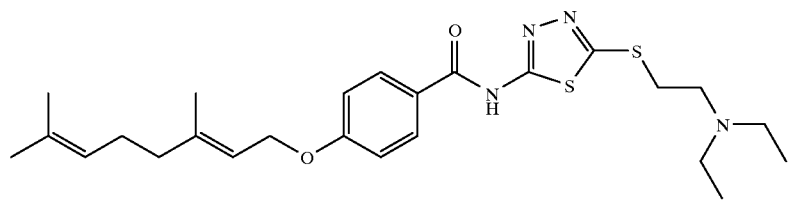

Example 11

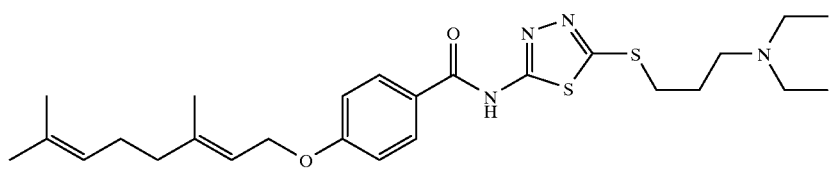

Example 12

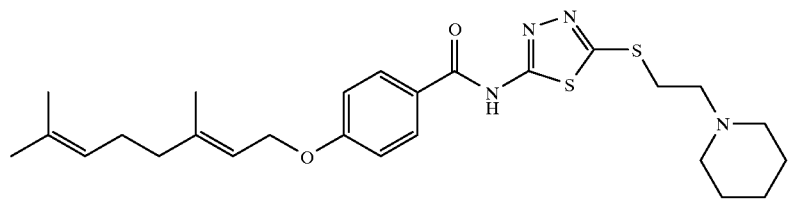

Example 13

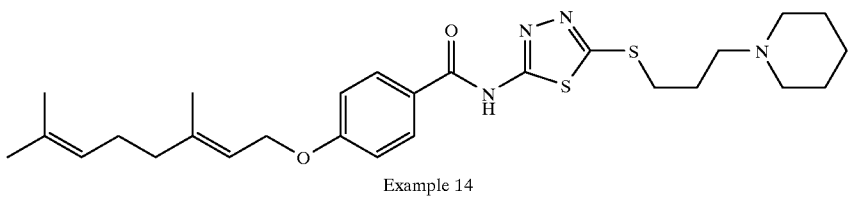

Example 14

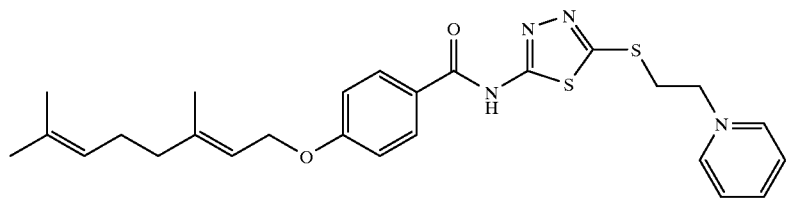

TABLE 3

| Example | Anti-ulcer Tests | | | | Tests for Safety | | |
|---|---|---|---|---|---|---|---|
| No. | WIS | VOL | TAO | CAP | PD | AT | MTT |
| 10 | 48 | 36 | 44 | 100 | 5 | 5 | 17 |
| 11 | 65 | | | 100 | | | 48 |
| 12 | 44 | | | 99 | 5 | 5 | 12 |
| 13 | 51 | | | 100 | | | 41 |
| 14 | 30 | | | 45 | 5 | 5 | −13 |

As can be seen from the foregoing Examples, the compound group 3 has high anti-ulcer effect. In particular, when $R_3$ is —$N(R_4)R_5$, excellent acid secretion inhibition effect can be exhibited. Further, these compounds are also excellent in safety.

Compound Group 4

The thiadiazoleamide derivatives in accordance with this group, as against that $R_3$ is —$N(R_4)R_5$ or a pyridyl group in the foregoing compound group 3, has a basic structure in which $R_3$ is a lower alkyl group or an aryl group as shown in Formula 5 described above.

As the thiadiazoleamide derivatives corresponding to this group, the following compounds were tested.

Example 15

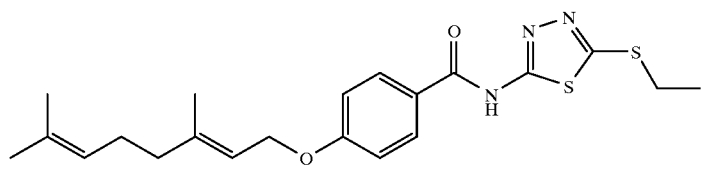

Example 16

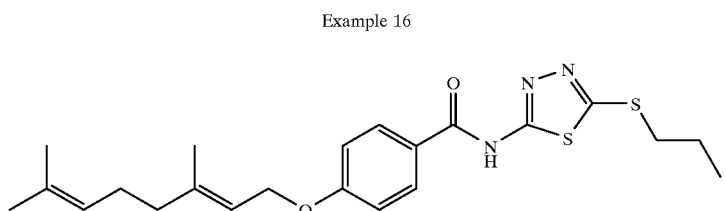

Example 17

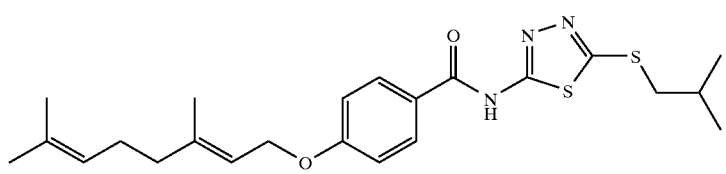

-continued

Example 18

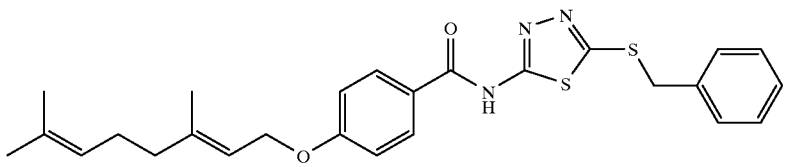

TABLE 4

| Example No. | Anti-ulcer Tests | | | | Tests for Safety | | |
|---|---|---|---|---|---|---|---|
| | WIS | VOL | TAO | CAP | PD | AT | MTT |
| 15 | 43 | 10 | 19 | 17 | 5 | 5 | 1 |
| 16 | 53 | | | | | | 14 |
| 17 | 46 | | | | | | −4 |
| 18 | 32 | | | | | | 18 |

As can be seen from the foregoing Examples, sufficient anti-ulcer effect can be obtained when $R_3$ is a lower alkyl group or an aryl group.

In the following, manufacturing method of the compounds in accordance with the above-mentioned Examples will be explained.

First, synthetic methods of intermediates used for manufacturing the Examples will be shown as Reference Examples 1 to 13.

Reference Example 1
Synthesis of 4-geranyloxybenzoic acid

Methyl 4-hydroxybenzoate (7.6 g), geranyl bromide (10.9 g), and potassium carbonate (13.8 g) were refluxed in acetone (80 ml) with stirring for 6 hours. The reaction mixture, with water added thereto, was extracted with chloroform. The extract was dried over sodium sulfate anhydride, and then concentrated under a vacuum. The residue was dissolved in methanol (50 ml) and the resulting mixture, with potassium hydroxide (3.9 g) and water (10 ml) added thereto, was stirred overnight at room temperature. The reaction mixture was neutralized with hydrochloric acid and then extracted with chloroform. The extract was dried over sodium sulfate anhydride, and then concentrated under a vacuum. The resulting solid was recrystallized from n-hexane/ethanol to yield 9.8 g of the aimed compound.

Reference Example 2
Synthesis of 3-piperidinomethylbenzoic acid

Methyl 3-methylbenzoate (45.0 g), N-bromosuccinimide (53.4 g) and a catalitic amount of azobisisobutyronitrile were refluxed in carbon tetrachloride (500 ml) with stirring for 24 hours. The reaction mixture was filtered and the filtrate was concentrated under a vacuum. The residue was purified by silica gel column chromatography (hexane:ethyl acetate=20:1), thereby yielding an oil. The oil was dissolved in dimethylformamide (1.5 l) and the mixture, with piperidine (63.2 g) and potassium carbonate (205 g) added thereto, was stirred all day and night at room temperature. The reaction mixture, with water added thereto, was extracted with ethyl acetate. The extract was dried over sodium sulfate anhydride, and then concentrated under a vacuum. The residue was purified by silica gel column chromatography (hexane:ethyl acetate=4:1), thereby yielding an oil. Potassium hydroxide (78.0 g), water (325 ml), and ethanol (325 ml) were added to the oil and the mixture was refluxed with stirring for 2 hours. After being neutralized with acetic acid, the reaction mixture, with chloroform added thereto, was filtered. The filtrate was concentrated under a vacuum. The resulting solid was washed with ethanol, thereby yielding 24.4 g of the aimed compound. The resulting solid was washed with ethanol, thereby yielding 24.4 g of the aimed compound.

Reference Example 3
Synthesis of 4-tert-butoxybenzoic acid

Ethyl 4-hydroxybenzoate (16.6 g), isobutene (25 g), and 95% sulfuric acid (0.5 ml) were stirred in dichloromethane (300 ml) overnight at 0° C. The reaction mixture was washed with 20% sodium carbonate aqueous solution, dried over sodium sulfate anhydride, and then concentrated under a vacuum. The residue was dissolved in ethanol (32 ml) and the solution, with potassium hydroxide (7.5 g) and water (6 ml) added thereto, was refluxed with stirring for 2 hours. The reaction mixture was neutralized with hydrochloric acid and then extracted with ethyl acetate. The extract was dried over sodium sulfate anhydride, and then concentrated under a vacuum. The resulting solid was recrystallized from ethyl acetate to yield 9.3 g of the aimed compound.

Reference Example 4
Synthesis of 4-tert-butylaminobenzoic acid

Ethyl 4-aminobenzoate (165 g) and 95% sulfuric acid (24.5 g) were refluxed in tert-butanol (560 ml) with stirring for 16 hours. The reaction mixture neutralized with 28% aqueous ammonia, was extracted with ethyl acetate. The extract was dried over sodium sulfate anhydride, and then concentrated under a vacuum. The residue was purified by silica gel column chromatography (hexane:ethyl acetate= 4:1), thereby yielding an oil. The oil was dissolved in ethanol (100 ml) and then potassium hydroxide (23.5 g) and water (20 ml) were added thereto. The mixture was refluxed with stirring for 2 hours, neutralized the mixture with hydrochloric acid , and then extracted with ethyl acetate. The extract was dried over sodium sulfate anhydride, and then concentrated under a vacuum. The resulting solid was recrystallized from ethyl acetate to yield 23.5 g of the aimed compound.

Reference Example 5
Synthesis of 4-(4-fluorobenzyloxy)-3-isobutylbenzoic acid Ethyl 4-hydroxybenzoate (50.0 g), methallyl chloride (32.6 g), and potassium carbonate (45.6 g) were refluxed in acetone (150 ml) with stirring for 40 hours. The reaction mixture was filtered, and then the filtrate was concentrated under a vacuum. The residue, with toluene (150 ml) added thereto, was washed with 2% sodium hydroxide aqueous solution and water successively, dried over sodium sulfate anhydride, and then concentrated under a vacuum to yield an oil. The oil was dissolved in N,N-dimethylaniline (80 ml) and the solution was refluxed with stirring for approximate 10 hours. The reaction mixture was acidified with concentrated hydrochloric acid while being cooled with ice, and then extracted with toluene. The extract was further extracted with 10% sodium hydroxide aqueous solution. The resulting water layer was acidified with concentrated hydrochloric acid, and then extracted with toluene. The extract was washed with water, dried over sodium sulfate anhydride, and then concentrated under a vacuum, thereby yielding a solid. The solid was dissolved in ethanol (580 ml) and the solution, with 10% palladium-charcoal (6.0 g) added thereto, was subjected to catalytic reduction in a hydrogen gas atmosphere. After the reaction mixture was filtered, the filtrate was concentrated under a vacuum, thereby yielding a solid. The solid was dissolved in acetone (350 ml) and the solution, with potassium carbonate (73.8 g) and 4-fluorobenzyl bromide (60.6 g) added thereto, was refluxed with stirring for 4 hours. The reaction mixture, with water added thereto, was extracted with ethyl acetate and concentrated under a vacuum. The residue, with water (120 ml), potassium hydroxide (29.9 g), and ethanol (250 ml) added thereto, was refluxed with stirring for 2 hours. The reaction mixture, with water added thereto, was neutralized with hydrochloric acid, and then extracted with ethyl acetate. The extract was washed with 10% hydrochloric acid and water successively, dried over sodium sulfate anhydride, and then concentrated under a vacuum. The resulting solid was recrystallized from n-hexane/ethanol to yield 71.5 g of the aimed compound.

Reference Example 6
Synthesis of 2-amino-5-diethylaminoethylthio-1,3,4-thiadiazole 2-Amino-5-mercapto-1,3,4-thiadiazole (13.3 g), diethylaminoethylchloridehydrochloride (17.2 g), and potassium hydroxide (11.2 g) were stirred in methanol (200 ml) overnight at room temperature. The reaction mixture was concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 19.0 g of the aimed compound.

Reference Example 7
Synthesis of 2-amino-5-diethylaminopropylthio-1,3,4-thiadiazole 1-Bromo-3-chloropropane (4.7 g), diethylamine (2.2 g), and potassium carbonate (8.3 g) were stirred in acetone (150 ml) for 4 days at room temperature. The reaction mixture, with water added thereto, was extracted with ethyl acetate. The extract was dried over sodium sulfate anhydride, and then concentrated under a vacuum. The residue was dissolved in methanol (50 ml) and the solution, with 2-amino-5-mercapto-1,3,4-thiadiazole (4.0 g) and potassium hydroxide (1.7 g) were added thereto, was refluxed with stirring for 12 hours. The reaction mixture was concentrated under a vacuum. The residue, with water added thereto, was extracted with chloroform. The extract was dried over sodium sulfate anhydride, and then concentrated under a vacuum. The resulting solid was purified by silica gel column chromatography (chloroform:methanol=3:1), thereby yielding 2.8 g of the aimed compound.

Reference Example 8
Synthesis of 2-amino-5-diisopropylaminoethylthio-1,3,4-thiadiazole 2-Amino-5-mercapto-1,3,4-thiadiazole (4.0 g), diisopropylaminoethylchloridehydrochloride (6.0 g), and potassium hydroxide (3.4 g) were stirred in methanol (100 ml) overnight at room temperature. The reaction mixture was concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 6.1 g of the aimed compound.

Reference Example 9
Synthesis of 2-amino-5-piperidinoethylthio-1,3,4-thiadiazole 2-Amino-5-mercapto-1,3,4-thiadiazole (4.0 g), dipiperidinoethylchloridehydrochloride (6.0 g), and potassium hydroxide (3.4 g) were stirred in methanol (100 ml) overnight at room temperature. The reaction mixture was concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 6.1 g of the aimed compound.

Reference Example 10
Synthesis of 2-amino-5-piperidinopropylthio-1,3,4-thiadiazole 2-Amino-5-mercapto-1,3,4-thiadiazole (13.3 g), piperidinopropylchloridehydrochloride (18.4 g), and potassium hydroxide (11.2 g) were stirred in methanol (300 ml) overnight at room temperature. The reaction mixture was concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 13.9 g of the aimed compound.

Reference Example 11
Synthesis of 2-amino-5-isobutylthio-1,3,4-thiadiazole

2-Amino-5-mercapto-1,3,4-thiadiazole (2.0 g), isobutyl bromide (2.1 g), and potassium hydroxide (0.8 g) were stirred in methanol (50 ml) overnight at room temperature. The reaction mixture was concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 1.1 g of the aimed compound.

Reference Example 12
Synthesis of 2-amino-5-benzylthio-1,3,4-thiadiazole

2-Amino-5-mercapto-1,3,4-thiadiazole (2.0 g), benzyl bromide (2.6 g), and potassium hydroxide (0.8 g) were stirred in methanol (50 ml) overnight at room temperature. The reaction mixture was concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 2.4 g of the aimed compound.

Reference Example 13
Synthesis of 2-amino-5-(2-piperidinomethyl) thio-1,3,4-thiadiazole 2-Amino-5-mercapto-1,3,4-thiadiazole (2.0 g), 2-chloromethylpyridine hydrochloride (2.5 g), and potassium hydroxide (1.7 g) were stirred in methanol (50 ml) overnight at room temperature. The reaction mixture was concentrated under a vacuum. The resulting solid was recrystallized from n-hexane/ethanol, thereby yielding 1.3 g of the aimed compound.

Example 1
Synthesis of 2-(4-isopropylbenzoyl)amino-5-diethylaminoethylthio-1,3,4-thiadiazole Sodium hydride (0.6 g) and 2-amino-5-diethylaminoethylthio-1,3,4-thiadiazole (2.3 g) were stirred in tetrahydrofuran (30 ml) for 30 minutes while being cooled with ice. 4-Isopropylbenzoic acid (1.6 g) and carbonyldiimidazole (1.8 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=20:1). The resulting solid was recrystallized from n-hexane/ethanol, thereby yielding 3.5 g of the aimed compound.

$^1$H-NMR(CDCl$_3$) δ:8.15 (2H, d, J=8.3 Hz), 7.39 (2H, d, J=8.3 Hz), 3.39 (2H, t, J=6.8 Hz), 3.00 (1H, s7, J=7.3 Hz), 2.85 (2H, t, J=6.8 Hz), 2.55 (4H, q, J=7.3 Hz), 1.30 (6H, d, J=7.3 Hz), 1.00 (6H, t, J=6.8 Hz).

Example 2
Synthesis of 2-(4-isopropylbenzoyl)amino-5-diisopropylaminoethylthio-1,3,4-thiadiazole Sodium hydride (0.6 g) and 2-amino-5-diisopropylaminoethylthio-1,3,4-thiadiazole (2.6 g) were stirred in tetrahydrofuran (30 ml) for 30 minutes while being cooled with ice. 4-Isopropylbenzoic acid (1.6 g) and carbonyldiimidazole (1.8 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=15:1). The resulting solid was recrystallized from n-hexane/ethanol, thereby yielding 2.3 g of the aimed compound.

$^1$H-NMR(CDCl$_3$) δ:12.40 (1H, bs), 8.17 (2H, d, J=8.8 Hz), 7.38 (2H, d, J=8.8 Hz), 3.35 (2H, t, J=6.8 Hz), 3.00 (3H, s7, J=6.8 Hz), 2.82 (2H, t, J=6.8 Hz), 1.30 (6H, d, J=6.8 Hz), 0.98 (12H, d, J=6.8 Hz).

Example 3
Synthesis of 2-(4-isopropylbenzoyl)amino-5-diisopropylaminoethylthio-1,3,4-thiadiazole hydrochloride 2-(4-Isopropylbenzoyl)amino-5-diisopropylaminoethylthio-1,3,4-thiadiazole (1.2 g) was dissolved in methanol (50 ml) and the solution, with hydrochloric acid-methanol (10 ml) added thereto, was stirred for 10 minutes at room temperature. The reaction mixture was concentrated under a vacuum. The resulting solid was recrystallized from n-hexane/ethanol, thereby yielding 1.3 g of the aimed compound.

$^1$H-NMR(CDCl$_3$) δ:11.78 (1H, bs), 8.13 (2H, d, J=8.3 Hz), 7.41 (2H, d, J=8.3 Hz), 4.02–3.93 (2H, m), 3.74–3.65 (2H, m), 3.48–3.36 (2H, m), 3.00 (2H, s7, J=6.8 Hz), 1.57 (6H, d, J=6.8 Hz), 1.46 (6H, d, J=6.8 Hz), 1.28 (12H, t, J=6.8 Hz).

Example 4
Synthesis of 2-(4-tert-butylbenzoyl)amino-5-diethylaminoethylthio-1,3,4-thiadiazole Sodium hydride (0.6 g) and 2-amino-5-diethylaminoethylthio-1,3,4-thiadiazole (2.3 g) were stirred in tetrahydrofuran (30 ml) for 30 minutes while being cooled with ice. 4-Tert-butylbenzoic acid (1.8 g) and carbonyldiimidazole (1.8 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=20:1). The resulting solid was recrystallized from n-hexane/ethanol, thereby yielding 1.7 g of the aimed compound.

$^1$H-NMR(CDCl$_3$) δ:8.17 (2H, d, J=8.3 Hz), 7.54 (2H, d, J=8.3 Hz), 3.40 (2H, t, J=6.8 Hz), 2.84 (2H, t, J=6.8 Hz), 2.55 (4H, q, J=7.3 Hz), 1.37 (12H, s), 1.00 (6H, t, J=7.3 Hz).

Example 5
Synthesis of 2-(4-tert-butylbenzoyl)amino-5-diisopropylaminoethylthio-1,3,4-thiadiazole Sodium hydride (0.6 g) and 2-amino-5-diisopropylaminoethylthio-1,3,4-thiadiazole (2.6 g) were stirred in tetrahydrofuran (30 ml) for 30 minutes while being cooled with ice. 4-Tert-butylbenzoic acid (1.8 g) and carbonyldiimidazole (1.8 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=15:1). The resulting solid was recrystallized from n-hexane/ethanol, thereby yielding 2.2 g of the aimed compound.

$^1$H-NMR(CDCl$_3$) δ:12.47 (1H, bs), 8.19 (2H, d, J=8.8 Hz), 7.54 (2H, d, J=8.8 Hz), 3.35 (2H, t, J=6.8 Hz), 3.00 (2H, s7, J=6.4 Hz), 2.83 (2H, t, J=6.8 Hz), 1.37 (9H, s), 0.97 (12H, d, J=6.4 Hz).

Example 6
Synthesis of 2-(3,5-di-tert-butylbenzoyl)amino-5-diethylaminoethylthio-1,3,4-thiadiazole Sodium hydride (0.6 g) and 2-amino-5-diethylaminoethylthio-1,3,4-thiadiazole (2.3 g) were stirred in tetrahydrofuran (30 ml) for 30 minutes while being cooled with ice. 3,5-Di-tert-butylbenzoic acid (2.3 g) and carbonyldiimidazole (1.8 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=20:1). The resulting solid was recrystallized from n-hexane/ethanol, thereby yielding 1.5 g of the aimed compound.

$^1$H-NMR(CDCl$_3$) δ:7.83 (1H, d, J=1.5 Hz), 7.69 (2H, t, J=1.5 Hz), 3.33 (2H, t, J=6.8 Hz), 2.83 (2H, t, J=6.8 Hz), 2.56 (4H, q, J=7.3 Hz), 1.35 (18H, s), 1.02 (6H, t, J=7.3 Hz).

Example 7
Synthesis of 2-(4-isopropyloxybenzoyl)amino-5-diethylaminoethylthio-1,3,4-thiadiazole Sodium hydride (0.6 g) and 2-amino-5-diethylaminoethylthio-1,3,4-thiadiazole (2.3 g) were stirred in tetrahydrofuran (30 ml) for 30 minutes while being cooled with ice. 4-Isopropyloxybenzoic acid (1.8 g) and carbonyldiimidazole (1.8 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=20:1). The resulting solid was recrystallized from n-hexane/ethanol, thereby yielding 2.4 g of the aimed compound.

$^1$H-NMR(CDCl$_3$) δ:8.22 (2H, d, J=8.8 Hz), 6.98 (2H, d, J=8.8 Hz), 4.67 (1H, s7, J=5.9 Hz), 3.37 (2H, t, J=6.8 Hz), 2.83 (2H, t, J=6.8 Hz), 2.54 (4H, q, J=7.3 Hz), 1.38 (6H, d, J=5.9 Hz), 1.00 (6H, t, J=7.3 Hz).

Example 8

Synthesis of 2-(4-tert-butoxybenzoyl)amino-5-diethylaminoethylthio-1,3,4-thiadiazole Sodium hydride (0.6 g) and 2-amino-5-diethylaininoethylthio-1,3,4-thiadiazole (2.3 g) were stirred in tetrahydrofuran (30 ml) for 30 minutes while being cooled with ice. 4-Tert butoxybenzoic acid (1.9 g) and carbonyldiimidazole (1.8 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=15:1). The resulting solid was recrystallized from n-hexane/ethanol, thereby yielding 3.1 g of the aimed compound.

$^1$H-NMR(CDCl$_3$) δ:8.16 (2H, d, J=8.8 Hz), 7.10 (2H, d, J=8.8 Hz), 3.37 (2H, t, J=6.8 Hz), 2.83 (2H, t, J=6.8 Hz), 2.56 (4H, q, J=7.3 Hz), 1.44 (9H, s), 1.01 (6H, t, J=7.3 Hz).

Example 9

Synthesis of 2-(4-tert-butyaminobenzoyl)amino-5-diethylaminoethylthio-1,3,4-thiadiazole 4-Tert-butylaminobenzoic acid (1.9 g) was added to thionyl chloride (20 ml) while being cooled with ice, and then stirred overnight at room temperature. The reaction mixture was concentrated under a vacuum. The residue, with 2-amino-5-diethylaminoethylthio-1,3,4-thiadiazole (2.3 g) and chloroform (30 ml) added thereto, was stirred for 3 hours at room temperature. The reaction mixture, with 1N sodium hydroxide aqueous solution added thereto, was extracted with ethyl acetate. The extract was dried over sodium sulfate anhydride, and then concentrated under a vacuum. The residue was purified by silica gel column chromatography (chloroform:methanol=15:1), thereby yielding 3.0 g of the aimed compound.

$^1$H-NMR(CDCl$_3$) δ:8.03 (2H, d, J=8.8 Hz), 6.70 (2H, d, J=8.8 Hz), 4.29 (1H, s), 3.36 (2H, t, J=6.8 Hz), 2.83 (2H, t, J=6.8 Hz), 2.55 (4H, q, J=7.3 Hz), 1.43 (9H, s), 1.00 (6H, t, J=7.3 Hz).

Example 10

Synthesis of 2-(4-geranyloxybenzoyl)amino-5-diethylaminoethylthio-1,3,4-thiadiazole Sodium hydride (0.4 g) and 2-amino-5-diethylaminoethylthio-1,3,4-thiadiazole (1.4 g) were stirred in tetrahydrofuran (30 ml) for 30 minutes while being cooled with ice. 4-Geranyloxybenzoic acid (1.6 g) and carbonyldiimidazole (1.1 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=20:1). The resulting solid was recrystallized from n-hexane/ethanol, thereby yielding 2.5 g of the aimed compound.

$^1$H-NMR(CDCl$_3$) δ:8.19 (2H, d, J=8.8 Hz), 7.01 (2H, d, J=8.8 Hz), 5.53–5.47 (1H, m), 5.18–5.06 (1H, m), 4.62 (2H, d, J=6.4 Hz), 3.26 (2H, t, J=7.3 Hz), 2.81 (2H, t, J=7.3 Hz), 2.58 (4H, t, J=7.3 Hz), 2.18–2.04 (4H, m), 1.76 (3H, s), 1.68 (3H, s), 1.61 (3H, s), 1.03 (6H, d, J=7.3 Hz).

Example 11

Synthesis of 2-(4-geranyloxybenzoyl)amino-5-diethylaminopropylthio-1,3,4-thiadiazole Sodium hydride (0.4 g) and 2-amino-5-diethylaminopropylthio-1,3,4-thiadiazole (1.5 g) were stirred in tetrahydrofuran (30 ml) for 30 minutes while being cooled with ice. 4-Geranyloxybenzoic acid (1.8 g) and carbonyldlimidazole (1.1 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=15:1). The resulting solid was recrystallized from n-hexane/ethanol, thereby yielding 3.1 g of the aimed compound.

$^1$H-NMR(CDCl$_3$) δ:8.18 (2H, d, J=8.8 Hz), 7.01 (2H, d, J=8.8 Hz), 5.54–5.44 (1H, m), 5.12–5.04 (1H, m), 4.62 (2H, d, J=6.4 Hz), 3.30 (2H, t, J=7.3 Hz), 2.56 (2H, t, J=7.3 Hz), 2.52 (4H, q, J=7.3 Hz), 2.20–2.14 (4H, m), 1.92 (2H, q5, J=7.3 Hz), 1.76 (3H, s), 1.67 (3H, s), 1.61 (3H, s), 1.01 (6H, t, J=7.3 Hz).

Example 12

Synthesis of 2-(4-geranyloxybenzoyl)amino-5-piperidinoethylthio-1,3,4-thiadiazole Sodium hydride (0.4 g) and 2-amino-5-piperidinoethylthio-1,3,4-thiadiazole (1.5 g) were stirred in tetrahydrofuran (30 ml) for 30 minutes while being cooled with ice. 4-Geranyloxybenzoic acid (1.6 g) and carbonyldiimidazole (1.1 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=20:1). The resulting solid was recrystallized from n-hexane/ethanol, thereby yielding 2.3 g of the aimed compound.

$^1$H-NMR(CDCl$_3$) δ:8.21 (2H, d, J=8.8 Hz), 7.01 (2H, d, J=8.8 Hz), 5.50 (1H, t, J=6.3 Hz), 5.12–5.06 (1H, m), 4.61 (2H, d, J=6.3 Hz), 3.40 (2H, t, J=7.3 Hz), 2.71 (2H, t, J=7.3 Hz), 2.44–2.32 (4H, m), 2.19–2.06 (4H, m), 1.76 (3H, s), 1.68 (3H, s), 1.61 (3H, s), 1.59–1.49 (4H, m), 1.46–1.34 (2H, m).

Example 13

Synthesis of 2-(4-geranyloxybenzoyl)amino-5-piperidinopropylthio-1,3,4-thiadiazole Sodium hydride (0.4 g) and 2-amino-5-piperidinopropylthio-1,3,4-thiadiazole (1.6 g) were stirred in tetrahydrofuran (30 ml) for 30 minutes while being cooled with ice. 4-Geranyloxybenzoic acid (1.6 g) and carbonyldiimidazole (1.1 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=10:1). The resulting solid was recrystallized from n-hexane/ethanol, hereby yielding 2.1 g of the aimed compound.

$^1$H-NMR(CDCl$_3$) δ:8.16 (2H, d, J=8.8 Hz), 7.01 (2H, d, J=8.8 Hz), 5.49 (1H, t, J=6.4 Hz), 5.14–5.06 (1H, m), 4.62 (2H, d, J=6.4 Hz), 3.29 (2H, t, J=7.3 Hz), 2.41 (2H, t, J=7.3 Hz), 2.33–2.22 (4H, m), 2.18–2.01 (4H, m), 1.95 (2H, q5, J=7.3 Hz), 1.76 (3H, s), 1.68 (3H, s), 1.61 (3H, s), 1.60–1.47 (4H, m), 1.45–1.33 (2H, m).

Example 14

Synthesis of 2-(4-geranyloxybenzoyl)amino-5-(2-pyridylmethyl)thio-1,3,4-thiadiazole Sodium hydride (0.3 g) and 2-amino-5-(2-pyridylmethyl)thio-1,3,4-thiadiazole (1.3 g) were stirred in tetrahydrofuran (30 ml) for 30 minutes while being cooled with ice. 4-Geranyloxybenzoic acid (1.5 g) and carbonyldiimidazole (1.0 ) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=20:1). The resulting solid was recrystallized from n-hexane/ethanol, thereby yielding 1.9 g of the aimed compound.

$^1$H-NMR(CDCl$_3$) δ:12.58 (1H, bs), 8.55 (1H, dd, J=1.0 Hz, 4.9 Hz), 8.22 (2H, d, J=8.8 Hz), 7.59 (1H, d, J=7.3 Hz), 7.29 (2H, d, J=7.3 Hz), 7.17 (1H, dd, J=1.0 Hz, 4.9 Hz), 7.01 (2H, d, J=8.8 Hz), 5.45 (1H, t, J=6.8 Hz), 5.08 (1H, t, J=6.8 Hz), 4.62 (2H, s), 4.57 (2H, t, J=6.8 Hz), 2.18–2.02 (4H, m), 1.71 (3H, s), 1.68 (3H, s), 1.60 (3H, s).

Example 15

Synthesis of 2-(4-geranyloxybenzoyl)amino-5-ethylthio-1,3,4-thiadiazole

4-Geranyloxybenzoic acid (2.2 g) and pyridine (1.0 g) were dissolved in benzene (40 ml). Thionyl chloride (1.4 g) was added to the solution while being cooled with ice and the mixture was stirred for 24 hours at room temperature. The reaction mixture was concentrated under a vacuum. Tetrahydrofuran (30 ml) and pyridine (1.3 g) were added to the residue. 2-Amino-5-ethylthio-1,3,4-thiadiazole (1.3 g) dissolved in tetrahydrofuran was added to the mixture while being cooled with ice and stirred for 3 days at room temperature. The reaction mixture was concentrated under a vacuum and the residue, with water added thereto, was extracted with ethyl acetate. The extract was dried over sodium sulfate anhydride, and then concentrated under a vacuum. The residue was purified by silica gel column chromatography (chloroform:methanol=15:1). The resulting solid was recrystallized from n-hexane/ethanol, thereby yielding 2.3 g of the aimed compound.

$^1$H-NMR(CDCl$_3$) δ:8.08 (2H, d, J=9.3 Hz), 7.01 (2H, d, J=9.3 Hz), 5.53–5.43 (1H, m), 5.14–5.04 (1H, m), 4.63 (2H, d, J=6.8 Hz), 3.27 (2H, q, J=7.3 Hz), 2.13–2.11 (4H, m), 1.76 (3H, s), 1.67 (3H, s), 1.61–1.59 (3H, m), 1.45 (3H, t, J=7.3 Hz).

Example 16

Synthesis of 2-(4-geranyloxybenzoyl)amino-5-propylthio-1,3,4-thiadiazole

Sodium hydride (0.6 g) and 2-amino-5-propylthio-1,3,4-thiadiazole (1.2 g) were stirred in tetrahydrofuran (30 ml) for 30 minutes while being cooled with ice. 4-Geranyloxybenzoic acid (1.9 g) and carbonyldiimidazole (1.3 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=15:1). The resulting solid was recrystallized from n-hexane/ethanol, thereby yielding 1.3 g of the aimed compound.

$^1$H-NMR(CDCl$_3$) δ:12.24 (1H, bs), 8.19 (2H, d, J=8.8 Hz), 7.01 (2H, d, J=8.8 Hz), 5.49 (1H, t, J=6.4 Hz), 5.12–5.04 (1H, m), 4.62 (2H, d, J=6.4 Hz), 3.22 (2H, d, J=7.3 Hz), 2.19–2.03 (4H, m), 1.80 (2H, s6, J=7.3 Hz), 1.75 (3H, s), 1.68 (3H, s), 1.61 (3H, s), 1.04 (3H, t, J=7.3 Hz).

Example 17

Synthesis of 2-(4-geranyloxybenzoyl)amino-5-isobutylthio-1,3,4-thiadiazole

Sodium hydride (0.4 g) and 2-amino-5-isobutylthio-1,3,4-thiadiazole (1.1 g) were stirred in tetrahydrofuran (30 ml) for 30 minutes while being cooled with ice. 4-Geranyloxybenzoic acid (1.6 g) and carbonyldiimidazole (1.1 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 1.9 g of the aimed compound.

$^1$H-NMR(CDCl$_3$) δ:12.46 (1H, bs), 8.21 (2H, d, J=8.8 Hz), 7.01 (2H, d, J=8.8 Hz), 5.49 (1H, t, J=6.4 Hz), 5.14–5.04 (1H, m), 4.62 (2H, d, J=6.4 Hz), 3.15 (2H, d, J=6.8 Hz), 2.26–2.12 (4H, m), 2.11 (1H, s7, J=6.8 Hz), 1.76 (3H, s), 1.68 (3H, s), 1.61 (3H, s), 1.04 (6H, d, J=6.8 Hz).

Example 18

Synthesis of 2-(4-geranyloxybenzoyl)amino-5-benzylthio-1,3,4-thiadiazole

Sodium hydride (0.6 g) and 2-amino-5-benzylthio-1,3,4-thiadiazole (1.6 g) were stirred in tetrahydrofuran (30 ml) for 30 minutes while being cooled with ice. 4-Geranyloxybenzoic acid (1.9 g) and carbonyldiimidazole (1.3 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The resulting solid was recrystallized from n-hexane/ethanol, thereby yielding 0.7 g of the aimed compound.

$^1$H-NMR(DMSO-d$_6$) δ:12.85 (1H, bs), 8.09 (2H, d, J=8.8 Hz), 7.42–7.19 (5H, m), 7.07 (2H, t, J=8.8 Hz), 5.44 (1H, t,

J=6.4 Hz), 5.10–5.01 (1H, m), 4.65 (2H, d, J=6.4 Hz), 4.50 (2H, s), 2.16–2.02 (4H, m), 1.72 (3H, s), 1.63 (3H, s), 1.57 (3H, s).

Example 19
Synthesis of 2-(3-piperidinomethylbenzoyl)amino-5-diethylaminoethylthio-1,3,4-thiadiazole

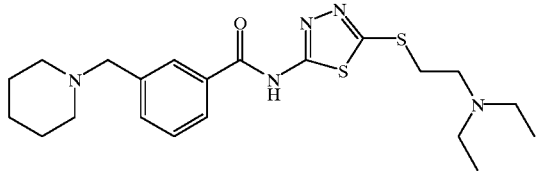

3-Piperidinomethylbenzoic acid (2.2 g) was added to thionyl chloride (20 ml) while being cooled with ice. After being stirred the mixture overnight at room temperature, the reaction mixture was concentrated under a vacuum. The residue, with 2-amino-5-diethylaminoethylthio-1,3,4-thiadiazole (2.3 g) and chloroform (30 ml) added thereto, was stirred for 3 hours at room temperature. The reaction mixture, with 1N sodium hydroxide aqueous solution added thereto, was extracted with ethyl acetate. The extract was dried over sodium sulfate anhydride and concentrated under a vacuum. The residue was purified by silica gel column chromatography (chloroform:methanol=15:1), thereby yielding 1.7 g of the aimed compound.

$^1$H-NMR(CDCl$_3$) δ:10.11 (1H, s), 8.12 (1H, d, J=8.3 Hz), 8.07 (1H, s), 7.61 (1H, d, J=8.3 Hz), 7.47 (1H, t, J=8.3 Hz), 3.56 (2H, s), 3.32 (2H, t, J=6.8 Hz), 2.81 (2H, t, J=6.8 Hz), 2.54 (4H, q, J=7.3 Hz), 2.48–2.34 (4H, m), 1.64–1.58 (4H, m), 1.56–1.38 (2H, m), 1.00 (6H, t, J=7.3 Hz).

Example 20
Synthesis of 2-{4-(4-fluorobenzyloxy)-3-isobutylbenzoyl}amino-5-diethylaminoethylthio-1,3,4-thiadiazole

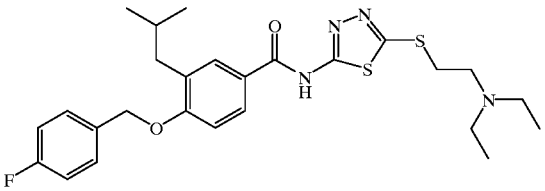

Sodium hydride (0.8 g) and 2-amino-5-diethylaminoethylthio-1,3,4-thiadiazole (3.3 g) were stirred in tetrahydrofuran (30 ml) for 30 minutes while being cooled with ice. 4-(4-Fluorobenzyloxybenzoic acid (2.1 g) and carbonyldiimidazole (1.3 g) were stirred in tetrahydrofuran (30 ml) for 30 minutes at room temperature and the mixture was added to the former reaction mixture. The mixture was stirred for 4 hours at room temperature, and then concentrated under a vacuum. The residue, with water added thereto, was extracted with ethyl acetate. The extract was dried over sodium sulfate anhydride, and then concentrated under a vacuum. The residue was purified by silica gel column chromatography (chloroform:methanol=15:1). The resulting solid was recrystallized from n-hexane/ethanol, thereby yielding 3.2 g of the aimed compound.

$^1$H-NMR(CDCl$_3$) δ:12.47 (1H, S), 8.06 (1H, d, J=8.8 Hz), 7.91 (1H, S), 7.40 (2H, d, J=8.8 Hz), 7.09 (2H, t, J=8.3 Hz), 7.01 (1H, d, J=8.3 Hz), 5.12 (2H, s), 3.90–3.86 (2H, m), 3.52–3.46 (2H, m), 3.35–3.13 (4H, m), 2.59 (2H, d, J=6.8 Hz), 1.87–2.05 (1H, m), 1.41 (6H, t, J=7.3 Hz), 0.91 (6H, d, J=6.4 Hz).

What is claimed is:

1. A thiadiazoleamide derivative or a salt thereof expressed by the following Formula 1:

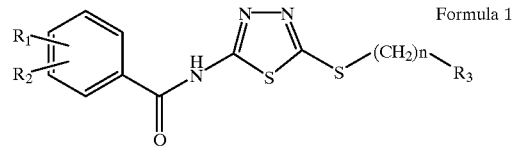

wherein each of $R_1$ and $R_2$ represents a hydrogen atom, a lower alkyl group, a lower alkoxy group, a lower alkylamino group or an alkenyloxy group; wherein when either $R_1$ or $R_2$ is a hydrogen atom, the other is not a hydrogen atom;

$R_3$ represents a lower alkyl group, an aryl group, a pyridyl group or —N($R_4$)$R_5$, wherein $R_4$ and $R_5$ represent lower alkyl groups or together represent a saturated heterocyclic ring having 4–8 members; wherein when $R_1$ or $R_2$ is a lower alkoxy group, $R_3$ is —N($R_4$)$R_5$ or a pyridyl group; and n represents an integer of 1–3.

2. A thiadiazoleamide or a salt thereof according to claim 1, wherein $R_1$ or $R_2$ is an alkenyloxy group.

3. A thiadiazoleamide derivative or a salt thereof according to claim 2, wherein said alkenyloxy group is a geranyloxy group.

4. A thiadiazoleamide derivative or a salt thereof according to claim 1, wherein $R_1$ or $R_2$ is a lower alkyl group.

5. A thiadiazoleamide derivative or a salt thereof according to claim 1, wherein $R_1$ or $R_2$ is a lower alkoxy group.

6. A thiadiazoleamide derivative or a salt thereof according to claim 1, wherein $R_3$ is —N($R_4$)$R_5$ or a pyridyl group; wherein $R_4$ and $R_5$ represent lower alkyl groups or together represent a saturated heterocyclic ring having 4–8 members.

7. A thiadiazoleamide derivative or a salt thereof according to claim 6, wherein $R_3$ is a piperidino group.

8. A thiadiazoleamide derivative or a salt thereof according to claim 1, wherein $R_1$ or $R_2$ is an alkenyloxy group or a lower alkyl group and $R_3$ is a lower alkyl group.

9. A thiadiazoleamide derivative or a salt thereof according to claim 1, wherein $R_1$ or $R_2$ is an alkenyloxy group or a lower alkyl group and $R_3$ is an aryl group.

10. A thiadiazoleamide derivative or a salt thereof according to claim 1, which is expressed by the following Formula 2:

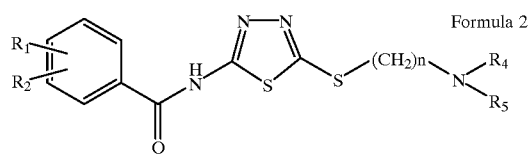

wherein each of $R_1$ and $R_2$ represents a hydrogen atom or a lower alkyl group; wherein when either $R_1$ or $R_2$ is a hydrogen atom, the other is a lower alkyl group;

$R_4$ and $R_5$ represent lower alkyl groups or together represent a saturated heterocyclic ring having 4–8 members; and n is an integer of 1 to 3.

11. A thiadiazoleamide derivative or a salt thereof according to claim 10, wherein either $R_1$ or $R_2$ is a hydrogen atom and n is 2.

12. A thiadiazoleamide derivative or a salt thereof according to claim 1, which is expressed by the following Formula 3:

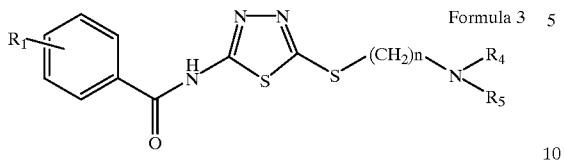

Formula 3 wherein $R_1$ represents a lower alkoxy group or a lower alkylamino group;

$R_4$ and $R_5$ represent lower alkyl groups or together represent a saturated heterocyclic ring having 4–8 members; and n is an integer of 1 to 3.

13. A thiadiazoleamide derivative or a salt thereof according to claim 12, wherein n is 2.

14. A thiadiazoleamide derivative or a salt thereof according to claim 1, which is expressed by the following Formula 4:

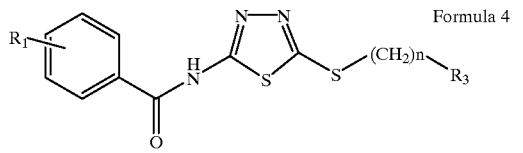

Formula 4 wherein $R_1$ represents an alkenyloxy group;

$R_3$ represents —$N(R_4)R_5$ or a pyridyl group, wherein $R_4$ and $R_5$ represent lower alkyl groups or together represent a saturated heterocyclic ring having 4–8 members; and n is an integer of 1 to 3.

15. A thiadiazoleamide derivative or a salt thereof according to claim 14, wherein $R_1$ is a geranyloxy group and $R_3$ is —$N(R_4)R_5$, wherein $R_4$ and $R_5$ represent lower alkyl groups or together represent a saturated heterocyclic ring having 4–8 members.

16. A thiadiazoleamide derivative or a salt thereof according to claim 1, which is expressed by the following Formula 5:

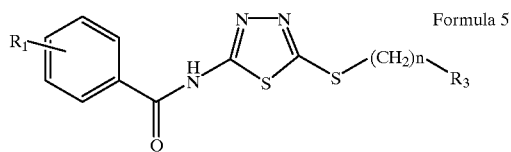

Formula 5 wherein $R_1$ represents an alkenyloxy group; and $R_3$ represents a lower alkyl group or an aryl group.

17. A thiadiazoleamide derivative or a salt thereof according to claim 16, wherein $R_1$ is a geranyloxy group.

18. An anti-ulcer drug comprising, as an effective ingredient, a thiadiazoleamide derivative or a pharmacologically acceptable salt thereof according to claim 1.

19. A method for treating peptic ulcers in mammals, which comprises administering an effective amount of a thiadiazoleamide derivative or a pharmacologically acceptable salt thereof according to claim 1 to said mammals.

20. A method according to claim 19, wherein said peptic ulcers are gastric ulcers in man.

21. A method for inhibiting acid secretion in stomach of mammals, which comprises administering an effective amount of a thiadiazoleamide derivative or a pharmacologically acceptable salt thereof according to claim 1 to said mammals.

22. A method for preventing peptic ulcers in mammals, which comprises administering an effective amount of a thiadiazoleamide derivative or a pharmacologically acceptable salt thereof according to claim 1 to said mammals.

23. A method according to claim 22, wherein said peptic ulcers are gastric ulcers in man.

\* \* \* \* \*